(12) United States Patent
Pappas et al.

(10) Patent No.: US 7,780,716 B2
(45) Date of Patent: Aug. 24, 2010

(54) DELIVERY SYSTEM FOR A MEDICAL DEVICE

(75) Inventors: Jeffrey Madsen Pappas, Santa Clara, CA (US); Daniel H. Shumer, San Jose, CA (US); Amelia Lasser, Menlo Park, CA (US); Jimmy Jen, Foster City, CA (US); Claus Volkl, Grosselfingen (DE); Juergen Anton Haun, Albstadt (DE)

(73) Assignee: Abbott Laboratories, Abbott Park, IL (US)

( * ) Notice: Subject to any disclaimer, the term of this patent is extended or adjusted under 35 U.S.C. 154(b) by 977 days.

(21) Appl. No.: 11/479,607

(22) Filed: Jun. 30, 2006

(65) Prior Publication Data

US 2007/0118201 A1 May 24, 2007

Related U.S. Application Data

(63) Continuation-in-part of application No. 10/932,964, filed on Sep. 2, 2004.

(60) Provisional application No. 60/499,075, filed on Sep. 2, 2003, provisional application No. 60/695,498, filed on Jun. 30, 2005.

(51) Int. Cl.
*A61F 2/84* (2006.01)
(52) U.S. Cl. ..................................... 623/1.11
(58) Field of Classification Search ............ 623/1.11, 623/1.12, 1.23; 606/108
See application file for complete search history.

(56) References Cited

U.S. PATENT DOCUMENTS

| | | | |
|---|---|---|---|
| 4,748,982 A | 6/1988 | Horzewski et al. |
| 4,921,483 A | 5/1990 | Wijay et al. |
| 5,254,107 A | 10/1993 | Soltesz |
| 5,370,655 A | 12/1994 | Burns |

(Continued)

FOREIGN PATENT DOCUMENTS

DE     1775056     3/1972

(Continued)

OTHER PUBLICATIONS

Non-Final Rejection mailed on Nov. 27, 2007 for U.S. Appl. No. 10/932,964.

(Continued)

*Primary Examiner*—Anhtuan T Nguyen
*Assistant Examiner*—Ryan J Severson
(74) *Attorney, Agent, or Firm*—Baker Botts LLP

(57) ABSTRACT

The invention is directed to a delivery system for delivering a medical device. The delivery system includes an inner member having a proximal end and a distal end. The inner member defines a longitudinal axis between the proximal end and the distal end. A tip is formed at the distal end of the inner member. A bumper is freely disposed on the inner member. The bumper has a proximal end and a distal end. A seat is defined between the tip and the distal end of the bumper. Additionally, a sheath is disposed about the inner member, the sheath having a proximal end and a distal end. The sheath is movable from a first sheath position substantially covering the seat, and a second sheath position axially offset to expose the seat. The invention also includes a handle in contact with the proximal end of the inner member.

20 Claims, 30 Drawing Sheets

U.S. PATENT DOCUMENTS

| | | | |
|---|---|---|---|
| 5,399,164 | A | 3/1995 | Snoke et al. |
| 5,405,378 | A | 4/1995 | Strecker |
| 5,445,646 | A | 8/1995 | Euteneuer et al. |
| 5,449,366 | A | 9/1995 | Li |
| 5,470,315 | A | 11/1995 | Adams |
| 5,477,856 | A | 12/1995 | Lundquist |
| 5,484,444 | A | 1/1996 | Braunschweiler et al. |
| 5,507,751 | A | 4/1996 | Goode et al. |
| 5,507,768 | A | 4/1996 | Lau et al. |
| 5,538,510 | A | 7/1996 | Fontirroche et al. |
| 5,542,924 | A | 8/1996 | Snoke et al. |
| 5,618,300 | A | 4/1997 | Marin et al. |
| 5,674,208 | A | 10/1997 | Berg et al. |
| 5,690,644 | A | 11/1997 | Yurek et al. |
| 5,709,703 | A | 1/1998 | Lukic et al. |
| 5,728,067 | A | 3/1998 | Enger |
| 5,733,267 | A | 3/1998 | Del Toro |
| 5,743,876 | A | 4/1998 | Swanson |
| 5,807,241 | A | 9/1998 | Heimberger |
| 5,891,154 | A | 4/1999 | Loeffler |
| 5,904,648 | A | 5/1999 | Arndt et al. |
| 5,906,619 | A | 5/1999 | Olson et al. |
| 5,910,145 | A | 6/1999 | Fischell et al. |
| 5,954,729 | A | 9/1999 | Bachmann et al. |
| 5,968,052 | A | 10/1999 | Sullivan, III et al. |
| 5,968,061 | A | 10/1999 | Mirza |
| 6,019,778 | A | 2/2000 | Wilson et al. |
| 6,102,890 | A | 8/2000 | Stivland et al. |
| 6,146,415 | A | 11/2000 | Fitz |
| 6,190,360 | B1 | 2/2001 | Iancea et al. |
| 6,203,550 | B1 | 3/2001 | Olson |
| 6,214,026 | B1 | 4/2001 | Lepak et al. |
| 6,238,837 | B1 | 5/2001 | Fan |
| 6,273,879 | B1 | 8/2001 | Keith et al. |
| 6,346,118 | B1 | 2/2002 | Baker et al. |
| 6,368,344 | B1 | 4/2002 | Fitz |
| 6,425,898 | B1 | 7/2002 | Wilson et al. |
| 6,471,673 | B1 | 10/2002 | Kastenhofer |
| 6,527,789 | B1 | 3/2003 | Lau et al. |
| 6,575,993 | B1 | 6/2003 | Yock |
| 6,579,246 | B2 | 6/2003 | Jacobsen et al. |
| 6,582,459 | B1 | 6/2003 | Lau et al. |
| 6,582,460 | B1 | 6/2003 | Cryer |
| 6,659,977 | B2 | 12/2003 | Kastenhofer |
| 6,755,854 | B2 * | 6/2004 | Gillick et al. ............... 623/1.11 |
| 2002/0045929 | A1 | 4/2002 | Diaz |
| 2002/0052642 | A1 | 5/2002 | Cox et al. |
| 2003/0028236 | A1 | 2/2003 | Gillick et al. |
| 2003/0040789 | A1 * | 2/2003 | Colgan et al. ............... 623/1.11 |
| 2003/0135162 | A1 | 7/2003 | Deyette et al. |
| 2003/0208262 | A1 | 11/2003 | Gaber |
| 2004/0006380 | A1 | 1/2004 | Buck et al. |
| 2005/0043618 | A1 | 2/2005 | Mansouri-Ruiz |
| 2005/0043713 | A1 | 2/2005 | Zhou |
| 2005/0060016 | A1 | 3/2005 | Wu et al. |
| 2005/0080476 | A1 | 4/2005 | Gunderson et al. |
| 2005/0182475 | A1 | 8/2005 | Jen et al. |
| 2007/0100422 | A1 | 5/2007 | Shumer et al. |
| 2007/0191864 | A1 | 8/2007 | Shumer et al. |
| 2007/0191865 | A1 | 8/2007 | Pappas |

FOREIGN PATENT DOCUMENTS

| | | |
|---|---|---|
| DE | 3219629 | 2/1986 |
| EP | 764423 | 3/1997 |
| EP | 1208816 | 5/2002 |
| EP | 1440671 | 2/2005 |
| EP | 1302178 | 3/2006 |
| WO | WO9904728 | 2/1999 |
| WO | WO0187180 | 11/2001 |

OTHER PUBLICATIONS

Response to the non-Final Rejection mailed on Nov. 27, 2007 filed on Feb. 27, 2007 for U.S. Appl. No. 10/932,964.

Final Rejection mailed on May 15, 2007 for U.S. Appl. No. 10/932,964.

Response to the Final Rejection mailed on May 15, 2007 filed on Jul. 13, 2007 for U.S. Appl. No. 10/932,964.

Advisory Action mailed on Jul. 24, 2007 for U.S. Appl. No. 10/932,964.

Request for Continued Examination (RCE) filed on Aug. 13, 2007 for U.S. Appl. No. 10/932,964.

Non-Final Rejection mailed on Oct. 31, 2007 for U.S. Appl. No. 10/932,964.

Response to the non-Final Rejection mailed on Oct. 31, 2007 filed on Jan. 25, 2008 for U.S. Appl. No. 10/932,964.

Final Rejection mailed on May 14, 2008 for U.S. Appl. No. 10/932,964.

Response to the Final Rejection mailed on May 14, 2008 filed on Aug. 14, 2008 for U.S. Appl. No. 10/932,964.

Advisory Action mailed on Sep. 11, 2008 for U.S. Appl. No. 10/932,964.

Notice of Appeal filed on Oct. 14, 2008 for U.S. Appl. No. 10/932,964.

Appeal Brief and Amendment after Brief filed on Jan. 14, 2009 for U.S. Appl. No. 10/932,964.

Appeal Brief filed on Mar. 4, 2009 for U.S. Appl. No. 10/932,964.

Examiner's Answer mailed on Jun. 9, 2009 for U.S. Appl. No. 10/932,964.

Reply Brief filed on Aug. 24, 2009 for U.S. Appl. No. 10/932,964.

Advisory Action mailed on Dec. 7, 2009 for U.S. Appl. No. 10/932,964.

Non-Final Rejection mailed on Nov. 3, 2009 for U.S. Appl. No. 11/479,644.

Non-Final Rejection mailed on Feb. 6, 2008 for U.S. Appl. No. 11/669,341.

Response to the non-Final Rejection mailed on Feb. 6, 2008 filed on May 1, 2008 for U.S. Appl. No. 11/669,341.

Final Rejection mailed on Jul. 16, 2008 for U.S. Appl. No. 11/669,341.

Response to the Final Rejection mailed on Jul. 16, 2008 filed on Oct. 16, 2008 for U.S. Appl. No. 11/669,341.

Advisory Action mailed on Nov. 17, 2008 for U.S. Appl. No. 11/669,341.

Request for Continued Examination (RCE) filed on Dec. 16, 2008 for U.S. Appl. No. 11/669,341.

Non-Final Rejection mailed on Mar. 5, 2009 for U.S. Appl. No. 11/669,341.

Notice of Appeal filed on Jun. 4, 2009 for U.S. Appl. No. 11/669,341.

Appeal Brief and Amendment after Brief filed on Aug. 4, 2009 for U.S. Appl. No. 11/669,341.

Advisory Action mailed on Sep. 8, 2009 for U.S. Appl. No. 11/669,341.

Examiner's Answer mailed on Nov. 16, 2009 for U.S. Appl. No. 11/669,341.

Non-Final Rejection mailed on Oct. 29, 2009 for U.S. Appl. No. 11/669,466.

* cited by examiner

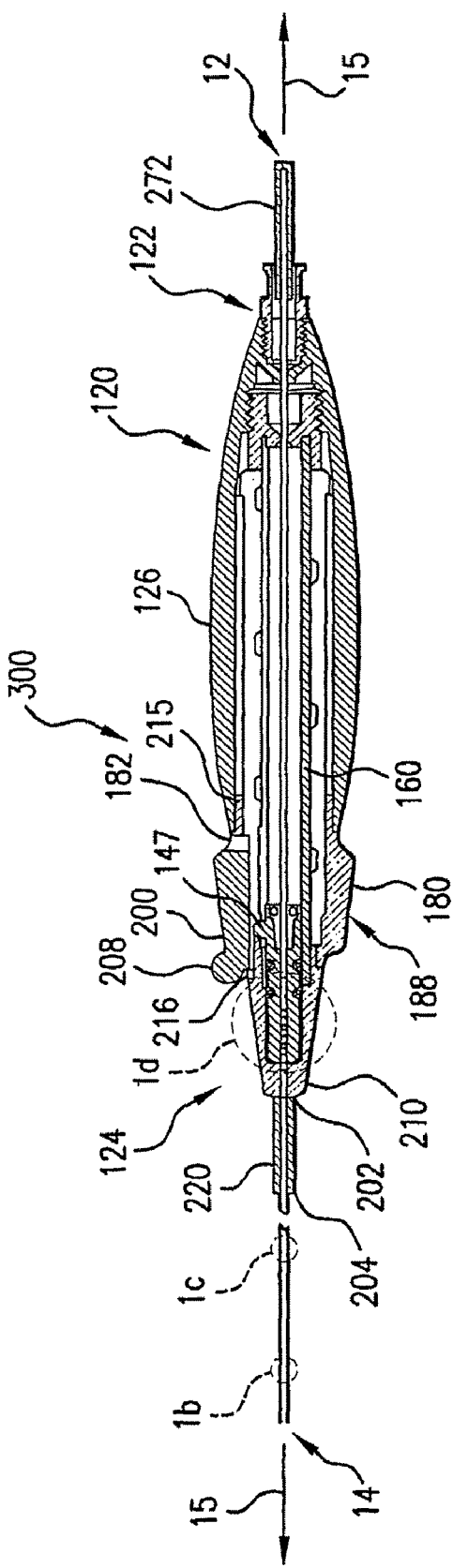
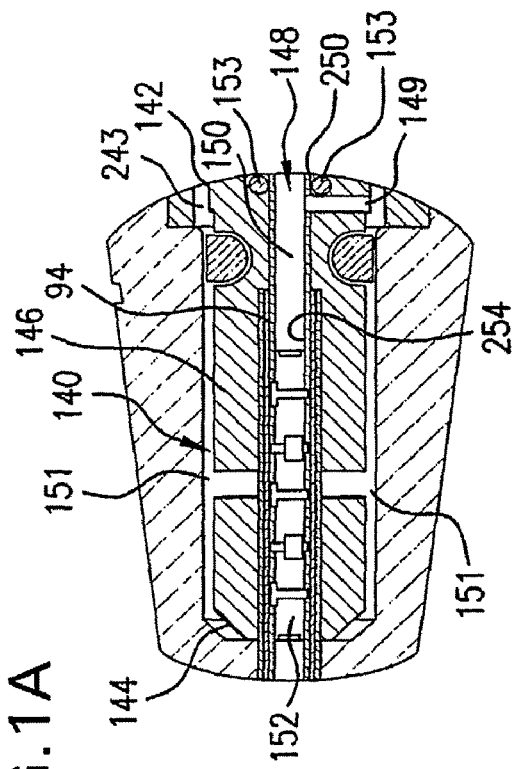
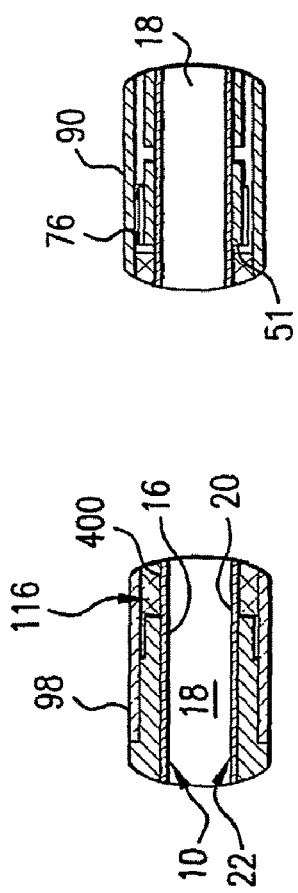
FIG.1A
FIG.1D
FIG.1C
FIG.1B

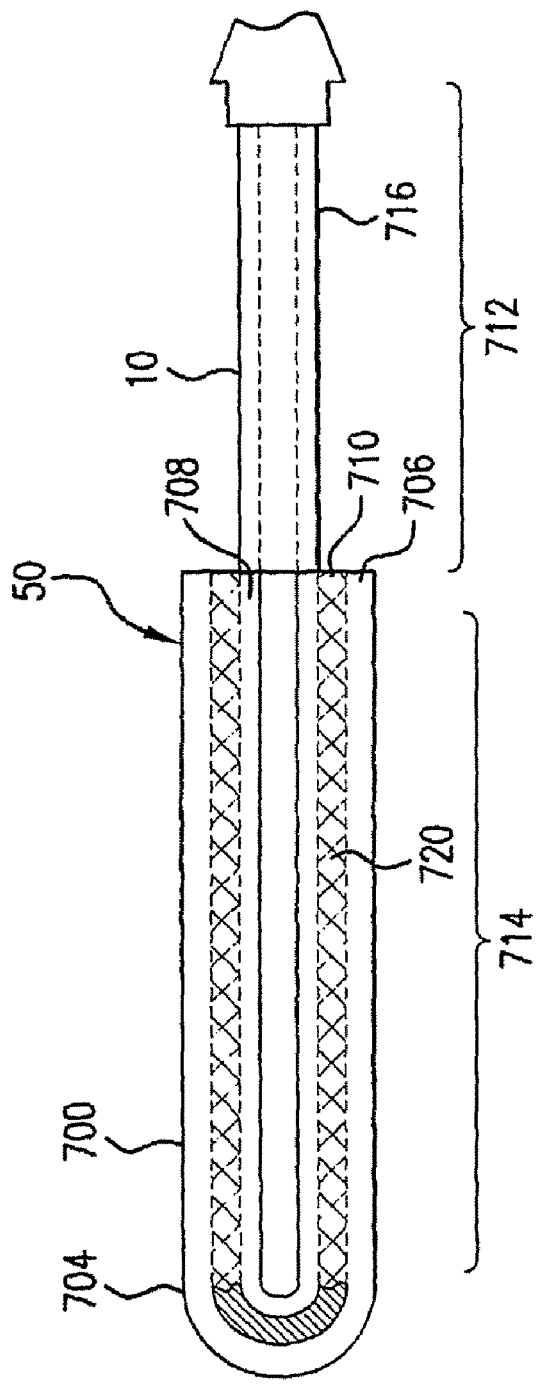
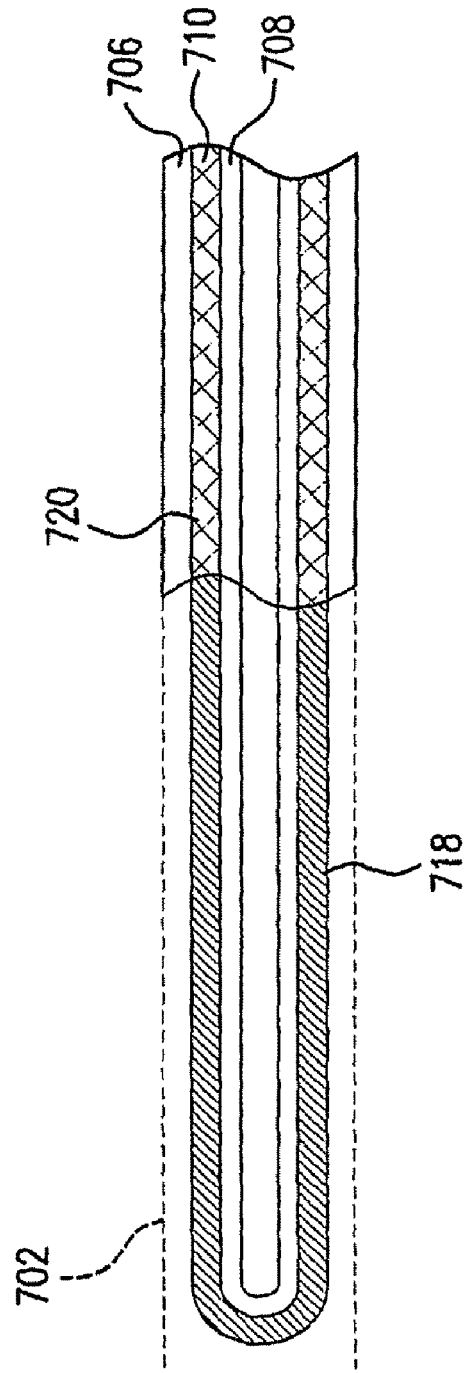
FIG.7D
FIG.7E

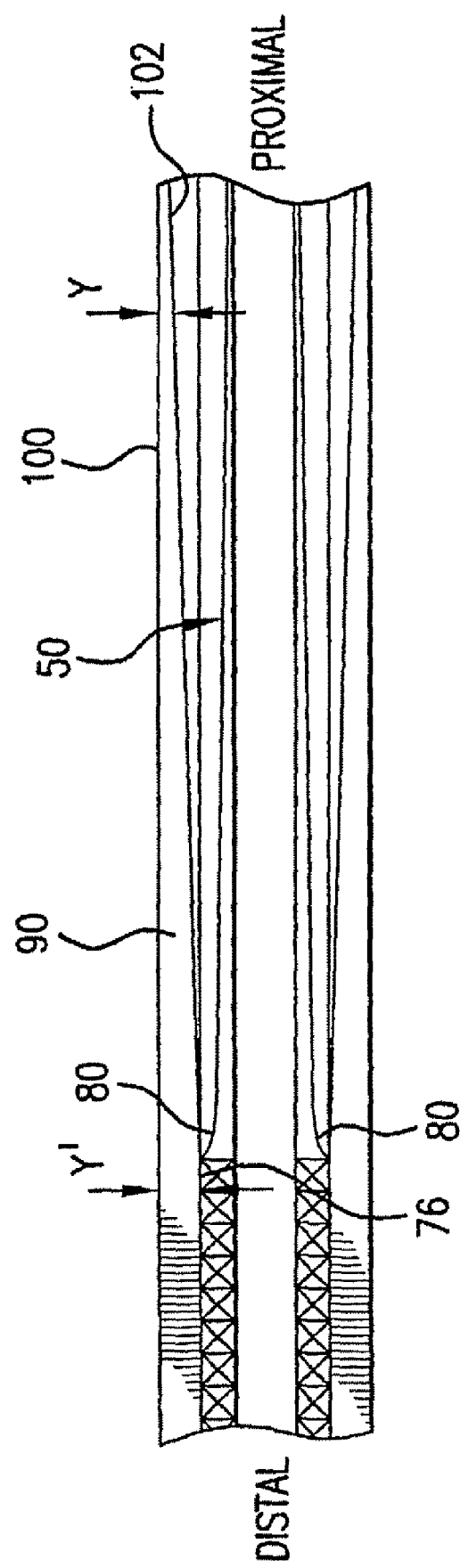

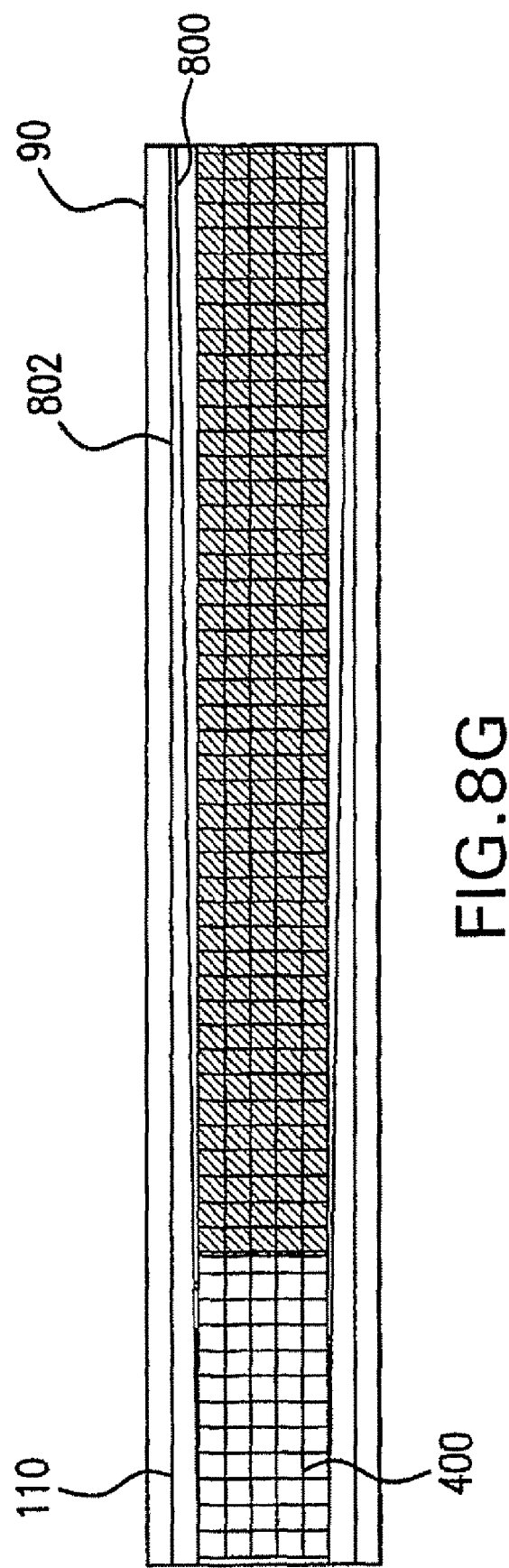

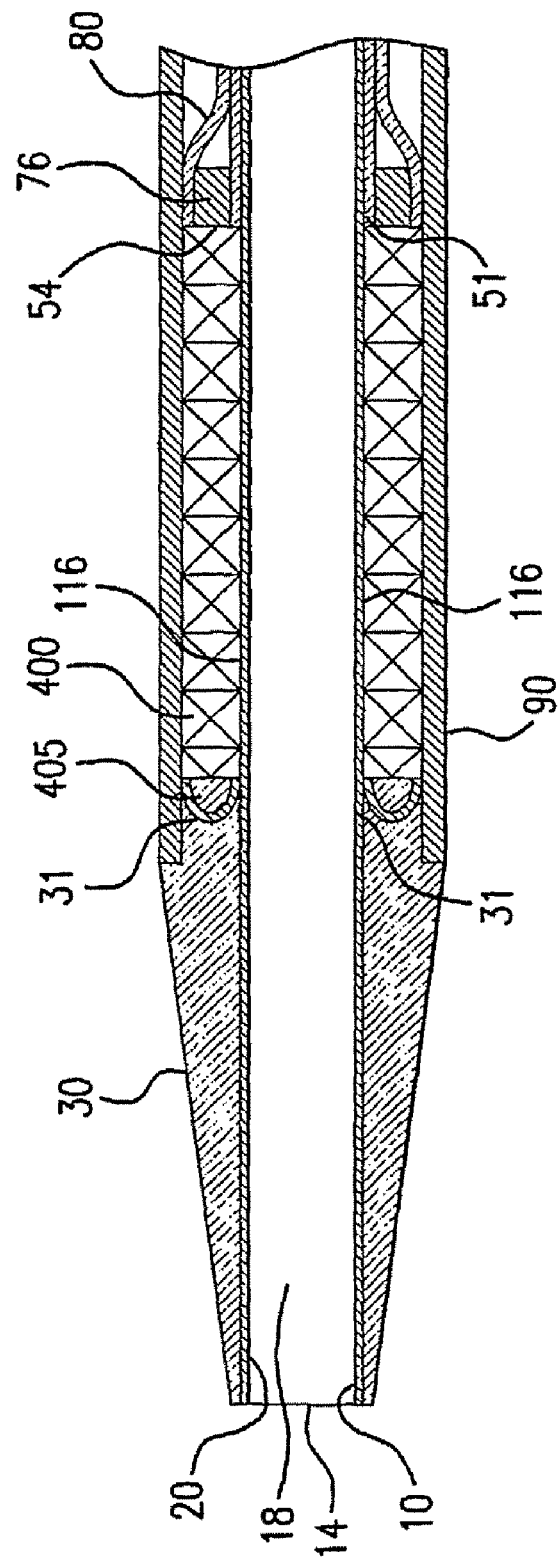

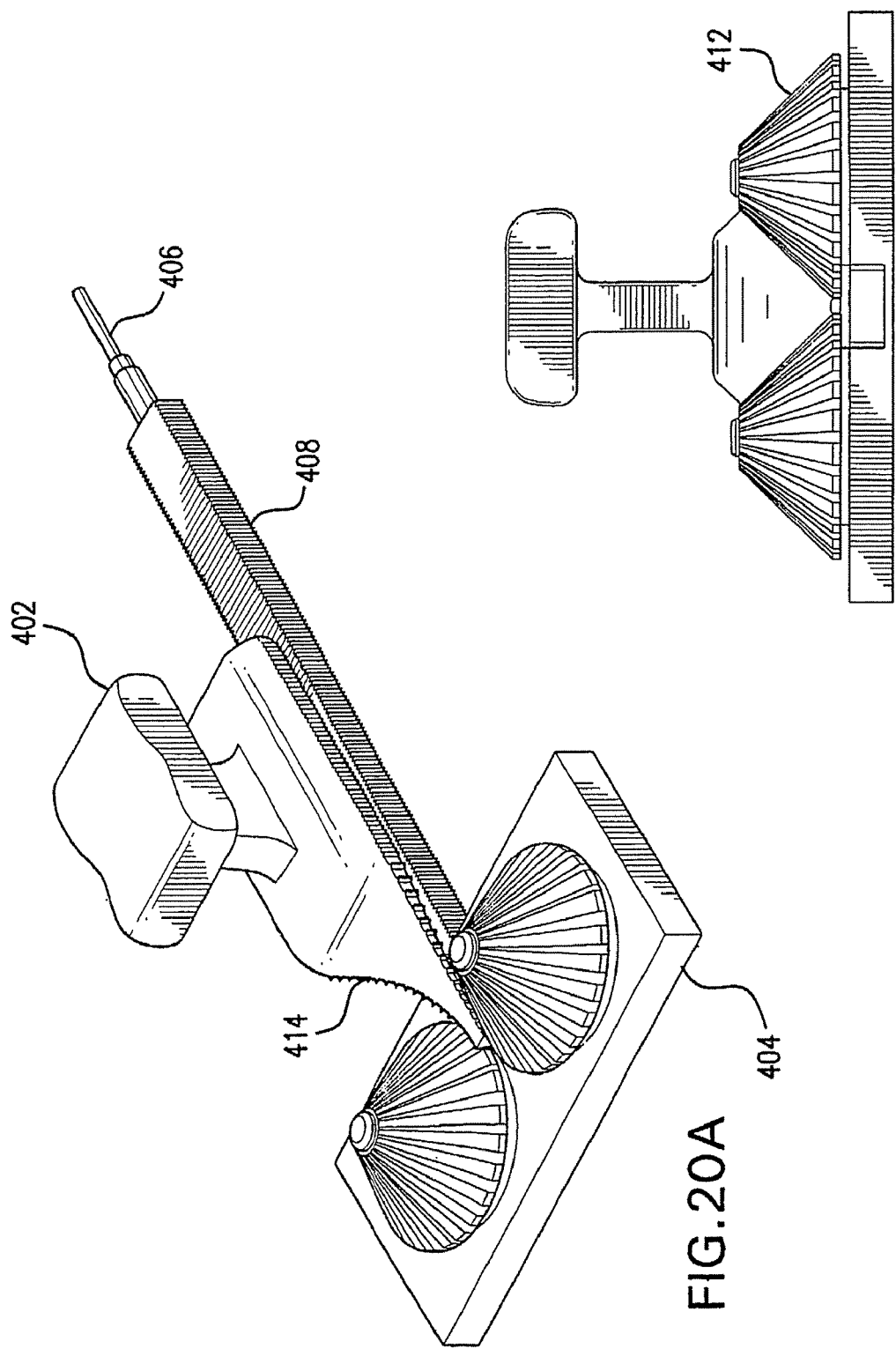

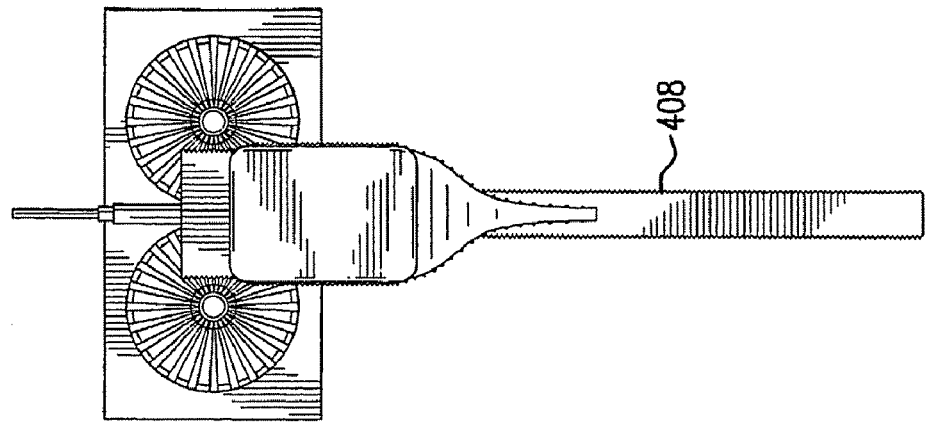
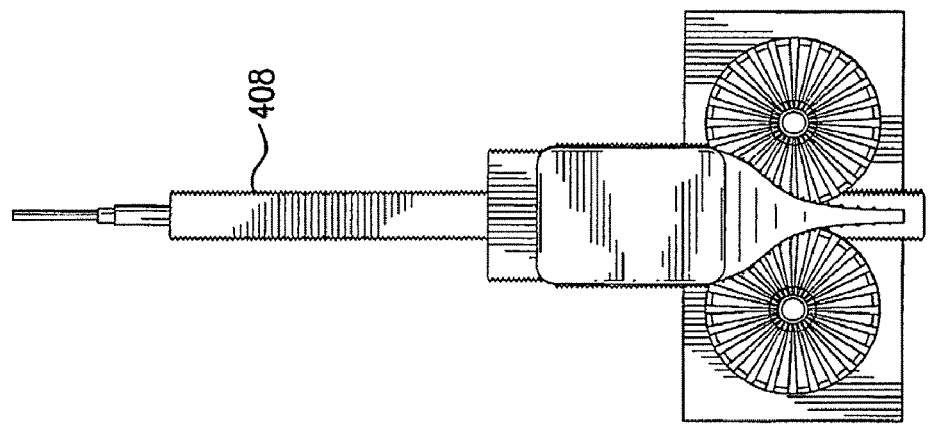
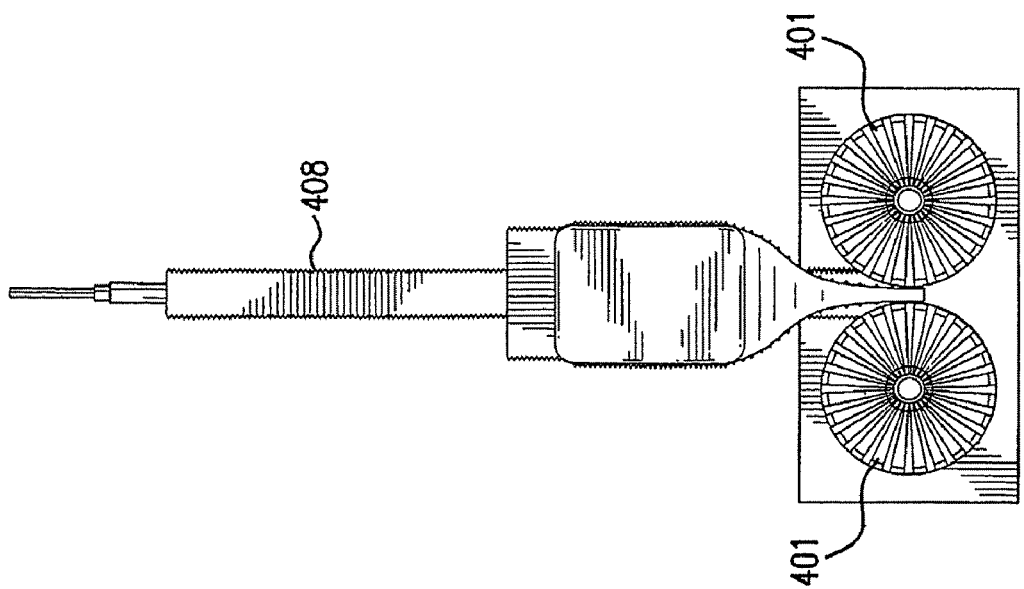

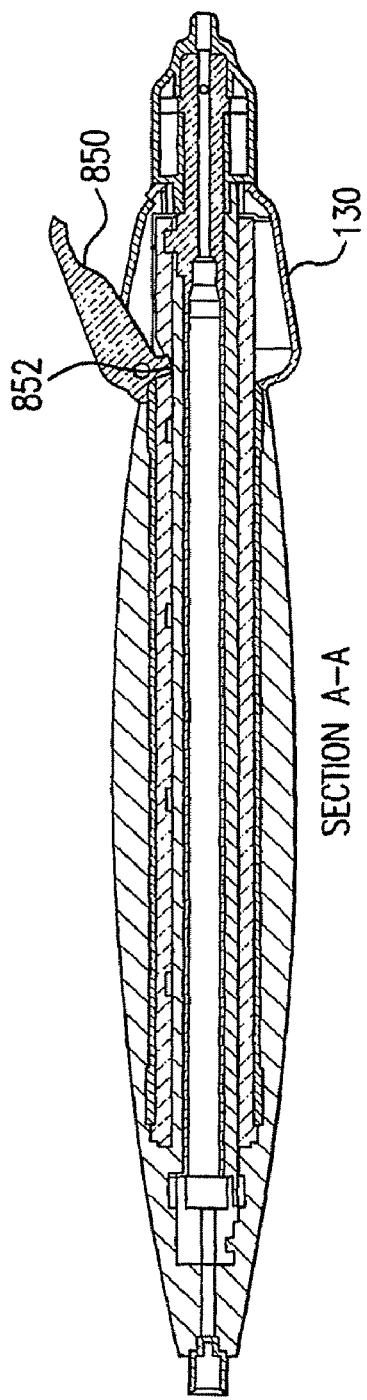
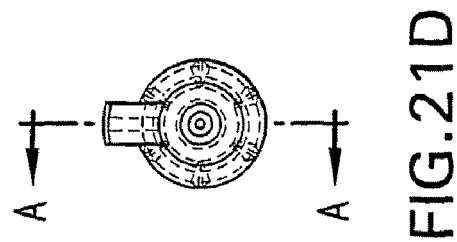
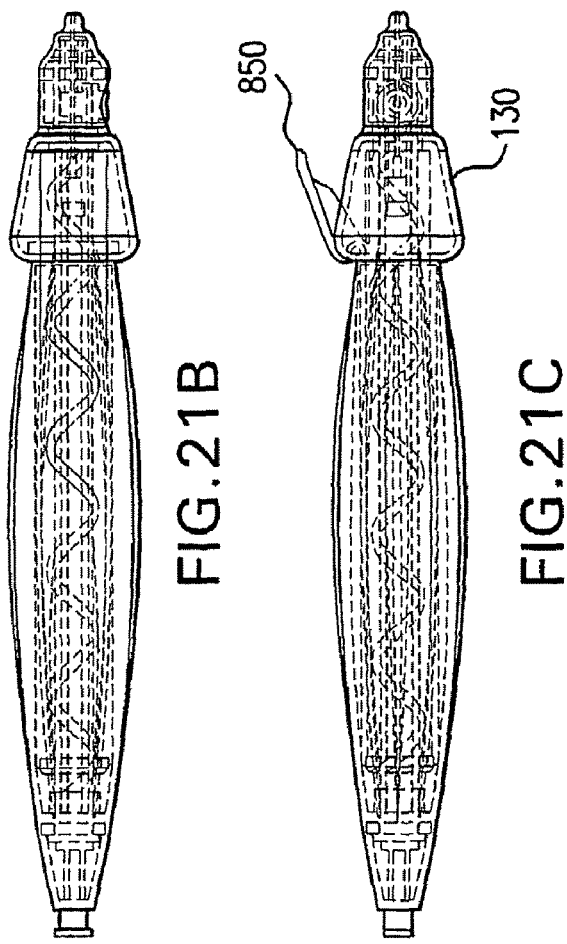
SECTION A-A
FIG.21A
FIG.21D
FIG.21B
FIG.21C

DELIVERY SYSTEM FOR A MEDICAL DEVICE

CROSS REFERENCE TO RELATED APPLICATION

The present application claims priority to U.S. Provisional Application Ser. No. 60/695,498 filed Jun. 30, 2005, and is a continuation-in-part of U.S. Ser. No. 10/932,964, filed Sep. 2, 2004, which claims priority to U.S. Provisional Application Ser. No. 60/499,075, filed Sep. 2, 2003 the entire contents of each is incorporated herein by reference.

FIELD OF THE INVENTION

The present invention relates to a delivery system for delivery of one or more medical devices, such as a stent, stent-graft or filter. Particularly, the present invention is directed to a delivery system including an inner member having a tip, a bumper freely disposed on the inner member, a sheath disposed about the inner member, and a handle attached to the inner member. The invention also includes a related method for assembling a delivery system.

DESCRIPTION OF RELATED ART

A variety of systems are known for intraluminal delivery of a medical device within a patient. However, there remains a need for continued improvement of such known delivery systems.

An example of such a system is described in U.S. Pat. No. 6,425,898 to Wilson et al., wherein a delivery system is provided having an inner member with a stop attached to the inner member. During deployment, the stop helps to "push" the stent out of the sheath during deployment, by preventing the stent from migrating proximally within the sheath during retraction of the sheath for stent deployment. As with other systems known in the art, the system described by Wilson does not permit re-adjustment of the different components of the mechanism after sterilization and shipment.

Conventional self-expanding stent delivery systems generally comprise a handle portion and an elongated shaft, wherein the stent is disposed within a delivery portion at the distal end of the shaft. To deploy the stent, an outer sheath is retracted relative to the stent, whereby the stent is released from its delivery configuration. Shortcomings of delivery systems that operate in this manner is that the sheath is generally pulled back in a 1 to 1 ratio with the user's input, which for a longer stent requires a large amount of user input to release the stent which may lead to incorrect placement. Additionally, when initially releasing the stent, it is desirable to slowly pull back the sheath until a certain amount of the stent has been delivered and is in contacted the vessel wall, wherein it is then desirable to quickly remove the sheath to prevent inadvertent movement of the stent.

Yet another shortcoming of present delivery systems is the amount of force that is required to remove the sheath from the stent. Therefore there is a need for an improved delivery system for self-expanding stents having reduced force requirements for delivery of a self-expanding stent.

There thus remains a continued need for an efficient and economic system for delivering a medical device that is easy to use and provides accurate stent placement. The present invention satisfies these and other needs.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention is directed to a delivery system for a medical device. The delivery system includes an inner member having a proximal end and a distal end. The inner member defines a longitudinal axis between the proximal end and the distal end. A tip is disposed at the distal end of the inner member. A bumper is disposed on the inner member. The bumper has a proximal end and a distal end. A seat is defined between the tip and the distal end of the bumper. The bumper includes a sleeve member, the sleeve member having a length and a tubular wall. A sheath is disposed about the inner member. The sheath has a proximal end and a distal end. The sheath is movable from a first sheath position substantially covering the seat, and a second sheath position axially offset to expose the seat. A handle is connected to the proximal end of the inner member. An actuator is disposed on the handle to move the sheath with respect to the inner member along the longitudinal axis from the first sheath position to the second sheath position.

The actuator includes a first gear to provide a first deployment rate for movement of the sheath and a second gear to provide a second deployment rate for the movement of the sheath.

In one embodiment, the first deployment rate is greater than the second deployment rate. The first gear is a sun gear. The second gear is at least one planetary gear. The first gear is be operatively coupled to a course adjust element, such as a thumbscrew, and the second gear may be operationally attached to a fine adjust element. Preferably, three planetary gears are provided.

In another aspect of the invention, the actuator is configured to move the sheath from the first sheath position to the second sheath position at a ratio greater than one to one. The ratio of the first gear and the second gear may be 3:1 or 2:1 or another desired ratio.

In another aspect of the invention, the inner member is a tubular member having a proximal end, a distal end, and a length therebetween.

In another aspect of the invention, the sleeve member of the bumper is formed of a flexible metallic element disposed along at least a portion of the length of the inner member. The bumper may further include an outer layer over at least a portion of the flexible metallic element. The bumper may define a first portion along the length of the inner member having a first diameter and a second portion along the length of the inner member having a second diameter. The first diameter is greater than the second diameter. The first diameter is defined by the inner member and bumper combined, and the second diameter is defined by the inner member. In another embodiment, the second diameter defines the seat. In yet another embodiment, the inner member defines a guidewire lumen along a length thereof. In another preferred embodiment, the inner member is formed of a lubricious material.

In another preferred embodiment, the outer layer is formed from a polymeric material. The flexible metallic element is a braid or coil element.

In another aspect of the invention, the bumper is freely disposed on the inner member.

In another aspect of the invention, the delivery system further includes a hypotube disposed about the inner member. The hypotube has a distal end and a proximal end. The distal end of the hypotube is proximal to the proximal end of the flexible metallic member.

In another aspect of the invention, the distal end of the bumper is configured to receive and radially constrain a proximal end of a stent disposed within the seat. In another embodiment, the distal end of the bumper includes a conical configuration, or the like. Alternatively, the distal end of the bumper includes at least one substantially rigid projection.

In accordance with another embodiment of the invention, the sheath includes an inner surface and an outer surface that define a wall thickness therebetween. The wall thickness is greater at the distal end than the proximal end. The wall thickness is tapered between the distal end and the proximal end.

In another embodiment, the sheath includes an outer wall and a liner. The liner has an inner surface and an outer surface defining a wall thickness therebetween. The wall thickness is greater at the distal end than the proximal end. The outer surface of the liner is secured to an inner surface of the outer wall. In another embodiment, the inner surface of the liner is lubricious.

In still another aspect of the invention, the delivery system also includes a lock having an unlocked position. The unlocked position permits movement of at least one of the actuator and sheath. The locked position prohibits movement of the at least one of the actuator and sheath.

In another embodiment, the lock includes a locking lever operationally engaged to the actuator and configured to releasibly lock at least one of the actuator and sheath, when in the locked position.

In yet another embodiment, the lock is operatively disposed to provide initial movement of the sheath when the lock is moved from the locked position to the unlocked position. The lock includes a cam to cooperate with the actuator to provide the initial movement. The locking lever is hingedly attached to the handle and further includes a detent configured to engage the actuator to inhibit movement of the sheath.

In another embodiment, the tip includes a stent retention feature. The retention feature including a recess to receive and radially constrain a distal end of a stent disposed in the seat.

In another embodiment of the invention, the delivery system for delivery of a medical device is configured to include an inner member having a proximal end and a distal end. The inner member defines a longitudinal axis between the two ends. A tip is disposed at the distal end of the inner member. A bumper is disposed on the inner member. The bumper has a proximal end and a distal end. A seat is defined between the tip and the distal end of the bumper. The bumper includes a sleeve member and the sleeve member has a length and a tubular wall. A sheath is disposed about the inner member. The sheath has a proximal end and a distal end. The sheath is movable from a first sheath position substantially covering the seat to a second sheath position axially offset to expose the seat. A handle is also provided to be in contact with the proximal end of the inner member.

An actuator is disposed on the handle and is coupled to a rack-and-pinion assembly to move the sheath with respect to the inner member along the longitudinal axis from the first sheath position to the second sheath position. The rack-and-pinion assembly is configured to increase a deployment rate of movement for the sheath during at least a portion of movement of the actuator.

In one embodiment, the ratio of movement of the sheath to movement of the actuator is greater than 1:1 during at least a portion of movement of the actuator. In another embodiment, the ratio of movement of the sheath to movement of the actuator varies. In yet another embodiment, the ratio of movement of the sheath to movement of the actuator is constant.

According to another embodiment, the rack-and-pinion assembly includes a first gear rack, a second gear rack and a pinion gear. The first rack is disposed at an angle less than ninety degrees relative to the second rack. The first gear rack is moveable relative the second gear rack and the pinion gear is operatively coupled to the first and second gear racks, respectively. In another embodiment, the first gear rack is coupled with the sheath. In another embodiment, the actuator includes a slider operatively coupled with the pinion gear. Movement of the slider engages the pinion gear along the second gear rack to rotate the pinion gear, which in turn engages the first gear rack for linear movement thereof.

In yet another embodiment, the first rack includes a plurality of gear teeth along a length and the second rack includes a plurality of gear teeth along a length. The first rack has a different number of teeth than the second rack.

In accordance with another embodiment of they delivery system, the first rack further comprises pins configured to be received within a track provided on the handle.

In another embodiment of the delivery system, the actuator includes a slider moveable in a linear direction. The slider has first and second extenders extending therefrom. Each extender includes a slot defined therein. The rack-and-pinion assembly includes a pinion gear having a first end, second end and a plurality of gear teeth formed therebetween. The first and second ends of the pinion gear slidingly engage a respective one of the slots defined in the first and second extenders. A first rack having a first end and a second end and a plurality of gear teeth is formed therebetweeen. The first rack is operatively coupled to the pinion gear. A second rack including a plurality of gear teeth disposed thereon is also provided. The plurality of gear teeth of the second rack operatively engage with the pinion gear. The engagement of the pinion gear along the second rack due to the movement of the slider results in movement of the first rack in the linear direction at a rate greater than the movement of the slider.

In another embodiment, the plurality of gear teeth disposed on the first rack have a pitch different than the plurality of gear teeth on the second rack. In yet another embodiment, the second rack includes a pair of elongate members. Each elongate member has a plurality of teeth in engagement with the pinion gear. In another embodiment, the second rack is arc-shaped. In another embodiment, the deployment rate of the sheath is at least twice the rate of movement of the actuator.

In another embodiment, the rack-and-pinion assembly includes a pinion having a plurality of teeth along its length and a rack gear having a circumferential surface and being rotatable about a center axis. The rack gear has a first gear pitch operatively coupled with the rack and a second gear pitch vertically displaced on a height of the circumferential surface. The actuator includes a slider having an elongate surface with a plurality of teeth therealong. The plurality of teeth of the slider are operatively coupled with the second gear pitch of the rack gear for rotation of the rack gear upon linear movement of the slider.

In another embodiment, the first gear pitch is defined by a first generally cylindrical portion of the rack gear. The rack gear has a first diameter and the second gear pitch is defined by a second generally cylindrical portion of the rack gear having a second diameter. The first diameter is greater than the second diameter. Rotation of the rack gear due to linear movement of the slider results in a greater rate of movement of the pinion.

In yet another embodiment, the pinion is operatively coupled to the sheath.

In another embodiment, the rack gear is a bevel gear that has a generally conical circumferential surface. The second gear pitch is varied along a height of the conical surface. The plurality of teeth of the slider are disposed at varied heights along the elongate surface. Linear movement of the slider results in varied engagement of the plurality of teeth along the height of the circumferential surface to vary the rate a rotation of the rack gear and the rate of movement of the rack.

In yet another embodiment, the plurality of teeth of the slider vary in pitch along a length of the elongate surface.

In another embodiment, the rack-and-pinion assembly includes a second rack gear and the pinion is disposed between the first and second rack gear.

In further accordance with the invention, a method for delivering two or more medical devices is provided. The method includes the steps of providing a delivery system for delivery of a medical device as described above, introducing the delivery system into a patient; delivering a first medical device; moving the inner member with respect to the sheath; and delivering a second medical device.

In accordance with a further aspect of the invention, a method can be provided wherein the first medical device and second medical device are delivered without removing the delivery system from the patient. Additionally or alternatively, the tip can be brought into contact with the distal end of the sheath during the inner member moving step. The method can further comprise the step of deploying a third medical device.

In further accordance with the invention a method for assembling a delivery system for delivery of a medical device is provided. The method includes the steps of providing a sheath and a bumper. The method includes the step of positioning the bumper into the sheath. The method further includes the steps of providing a medical device having a proximal end and a distal end and disposing the medical device in the sheath distal to the bumper, providing an inner member, and placing the inner member through the distal end of the sheath, and attaching a handle to the inner member.

In further accordance with the invention, the bumper positioning step can include positioning the bumper into the distal end of the sheath. The inner member placing step can also include positioning the proximal end of the inner member through the medical device and the bumper.

In further accordance with the invention, the method can entail the step of applying a lubricious material to the distal end of the sheath. In accordance with this aspect of the invention, the lubricious material application step can include the step of applying a pressurized fluid to the proximal end of the sheath to cause the lubricious material to coat the medical device.

In accordance with another aspect of the invention, the method can further include the steps of providing a tip and positioning the tip on the distal end of the inner member. The inventive method can also include the step of applying tension to the proximal end of the inner member to cause the distal end of the sheath to come into physical contact with the tip.

In accordance with still another aspect of the invention, the bumper providing step can include the steps of providing a sleeve member, providing a radiopaque portion, and placing the radiopaque portion on the sleeve member. The bumper providing step can also include the steps of providing a covering member and disposing the covering member on the sleeve member and radiopaque portion.

In still further accordance with the invention, the method can further comprise the steps of providing an actuator and an adjustment member, and adjusting the position of the inner member relative to the sheath using the adjustment member.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the delivery system, and method of the invention. Together with the description, the drawing serves to explain the principles of the invention.

BRIEF DESCRIPTION OF THE DRAWINGS

FIG. 1(a) is a cross sectional view of a first representative embodiment of the delivery system for delivering a medical device in accordance with the present invention.

FIGS 1(b)-1(d) are enlarged views of selected details of FIG. 1(a)

FIGS. 7D and 7E are partial cross-sectional views of an alternative embodiment of a delivery system in accordance with the present invention.

FIGS. 8F to 8G are cross-sectional views of alternative embodiments of a sheath in accordance with the present invention.

FIGS. 9B-D are cross-sectional views of a distal portion of the device illustrating stent retention mechanisms in accordance with the present invention.

FIGS. 20a through 20i are partial views of an alternative embodiment of a sheath retraction mechanism in accordance with the present invention.

FIGS. 21a through 21d are partial views of an alternative embodiment of a lock in accordance with the present invention.

DETAILED DESCRIPTION OF THE PREFERRED EMBODIMENTS

Figure 2:
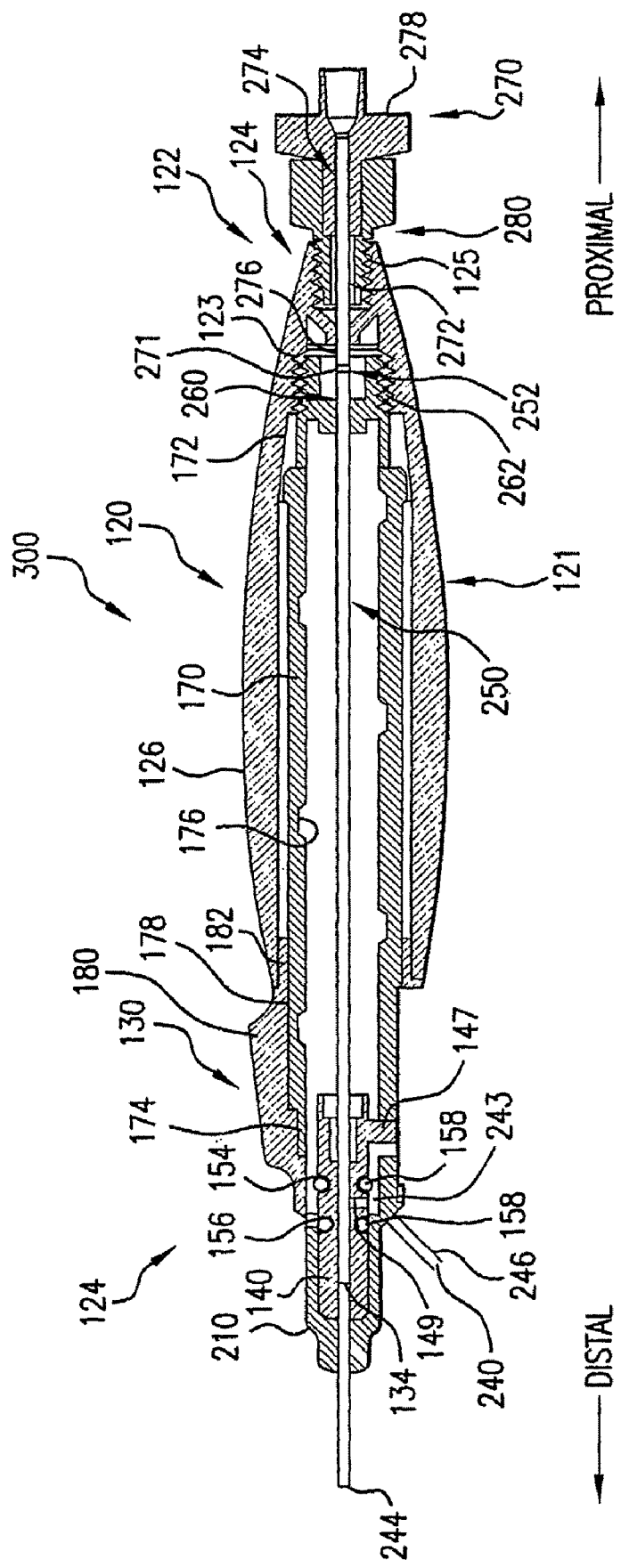
FIG. 2 is an alternative partial cross sectional view of a proximal portion of the device of FIG. 1.
Figure 3:
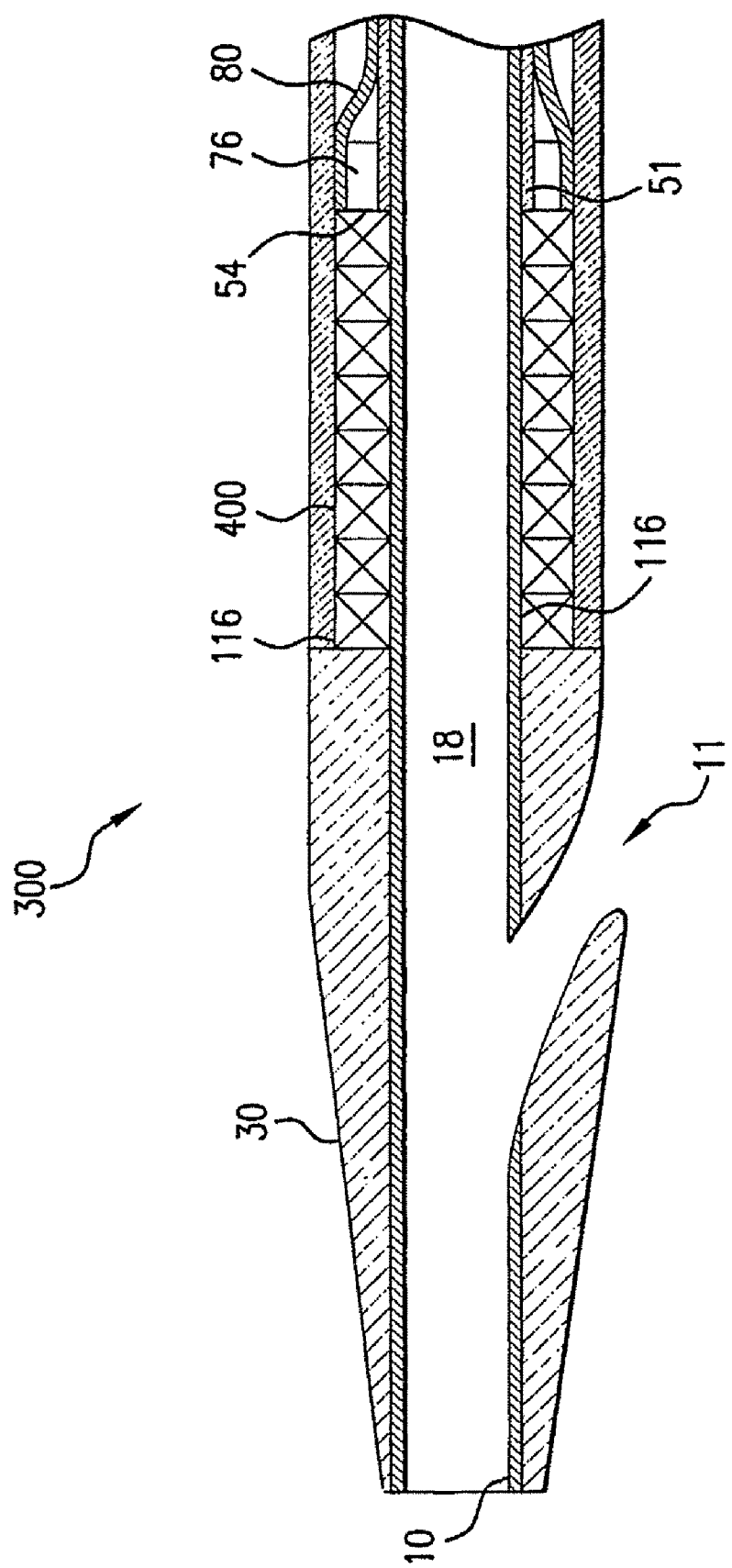
FIG. 3 is an enlarged partial cross sectional view of a distal portion of an alternative embodiment of a delivery system in accordance with the present invention.

Reference will now be made in detail to the present preferred embodiments of the invention, examples of which are illustrated in the accompanying drawings. The method and corresponding steps of the invention will be described in conjunction with the detailed description of the apparatus. The methods and apparatus presented herein are used for delivering a medical device, such as a stent, stent graft or filter, to a desired location in a patient.

In accordance with the invention, it is possible and desired to provide a system for delivering such devices that is relatively inexpensive to manufacture and easy to use.

For purpose of explanation and illustration, and not limitation, an exemplary embodiment of the delivery system for a medical device in accordance with the invention is shown in FIGS. 1(a)-1(d) and is designated generally by reference character 1. This exemplary embodiment or portions thereof is also depicted in FIGS. 2, 4-6(a), 7-9, and 13-14(a). Additional embodiments are shown in FIGS. 3, 6(b), 10-12 14(b)-14(c) and 15 for purpose of illustration and not limitation.

A variety of types of medical devices are suitable for delivery by the delivery system of the present invention. For purpose of illustration and not limitation, medical device 400 is depicted herein as a self-expanding stent. Such devices are generally well known in the art. However, the delivery system 300 of the present invention is not limited to the delivery of self-expanding stents. Other devices may also be used. For example, stent-grafts, coils, filters, balloon expandable stents, stent grafts, and embolic protection devices may be delivered within a patient's vasculature using the delivery system 300 of the present invention. Other devices such as a prosthesis retrieval mechanism may also be delivered with the delivery system 300 to a predetermined location in a patient's luminal system. Moreover, combinations of medical devices and/or beneficial agents can also be delivered using the device of the present invention. For example, multiple stents and/or a combination of stents and embolic protection devices and/or beneficial agents can be delivered using delivery system 300 of the present invention, as described in detail below.

The delivery system in accordance with the present invention includes an inner member having a proximal end and a distal end, generally defining a longitudinal axis therebetween.

Figure 9A:
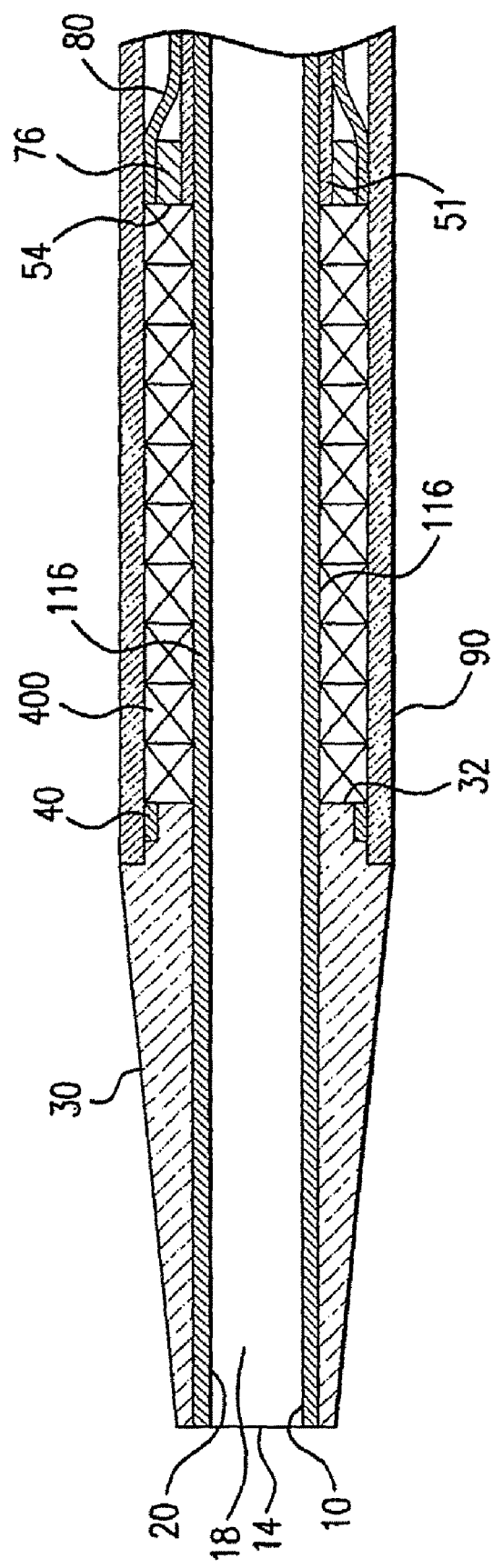
FIG. 9A is an enlarged cross sectional view of a distal portion of the device of FIG. 1.
Figure 10:
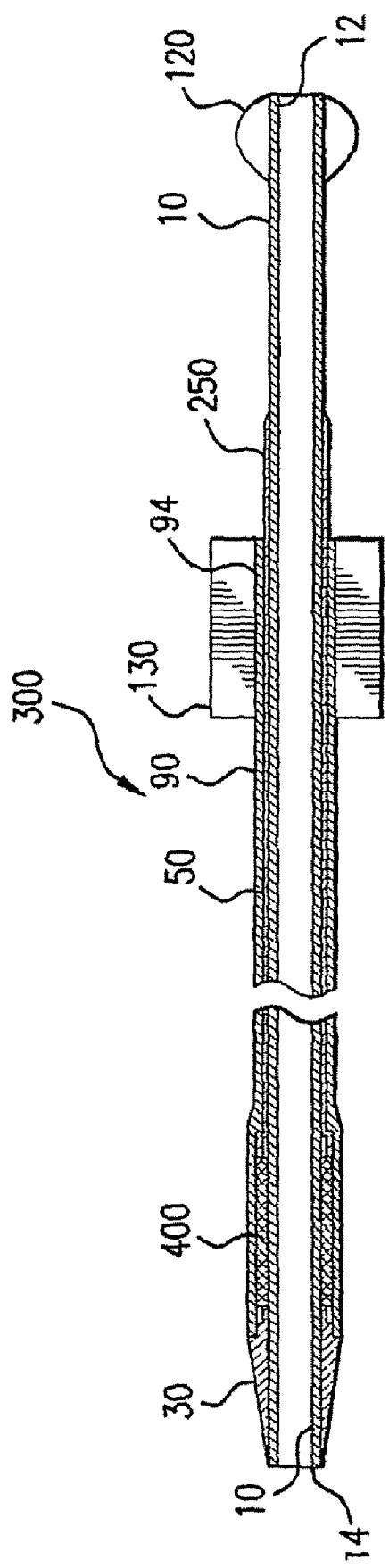
FIG. 10 is a cross sectional view of an alternative embodiment of a delivery system in accordance with the present invention.

For purposes of illustration and not limitation, the inner member 10 is schematically depicted in FIGS. 1B, 9 and 10. Inner member 10 is generally a longitudinal elongate member having a proximal end 12 and a distal end 14 and a length therebetween. Preferably, inner member is a tubular member having a cylindrical wall 16 that defines a lumen 18 therethrough and having an inner surface 20 (See FIG. 1(b)). Lumen 18 preferably traverses the entirety of the length of inner member 10, and is configured to permit passage of a guidewire (not shown) therethrough. Alternatively, the lumen may be defined only in the distal portion of the inner member to facilitate rapid exchange of a guidewire as described further below.

Inner member 10 is preferably made from a polymeric material such as PEEK and preferably traverses substantially the entire length of delivery system 300. However, any of a variety of materials can be used for inner member 10. For example, inner member could be made from other polymers such as PTFE, PVDF, Kynar, or polyethylene of various suitable densities. Alternatively, inner member could be made from a metallic material, such as Nitinol or stainless steel. As a further alternative, inner member 10 can be a composite member comprising a fabrication of several different materials, such as a co-extrusion of different polymers, or fiber-reinforced composite material such as fiber-reinforced resin material.

In accordance with an exemplary embodiment of the invention, suitable dimensions for inner member 10 include a length of about 60 inches, an external diameter of about 0.045 inches and an internal diameter of about 0.038 inches. It is recognized, however, that the dimensions will depend on the intended or desired applications for the delivery system and the above dimensions should not be considered limiting in any manner.

Surface 20 of lumen 18 is preferably provided with a lubricious coating 22 thereon, such as silicone or a suitable hydrophilic material to facilitate passage of a guidewire therein. However, a variety of coatings and/or surface treatments can be used.

A variety of different configurations may be used for inner member 10. With specific reference to FIG. 3, in accordance with another exemplary embodiment of the invention, a guidewire proximal port is provided a relatively short distance along the length of inner member 10. In accordance with this aspect of the invention, inner member 10 defines a guidewire exit port 11 near the distal end of delivery system 300 to permit entry and exit of a guidewire (not shown). A delivery system made in accordance with this aspect of the invention would be suitable for use as a rapid exchange catheter, which offers the advantage of not having to use an elongated guidewire or guidewire extension, so as to further simplify the delivery procedure.

Further in accordance with the invention, a tip is located at or proximate the distal end 14 of inner member 10. FIG. 9A shows an exemplary embodiment of a tip in accordance with the invention. Preferably, the tip provides an enlarged cross dimension at or proximate the distal end of the inner member, as will be described.

Figure 4:
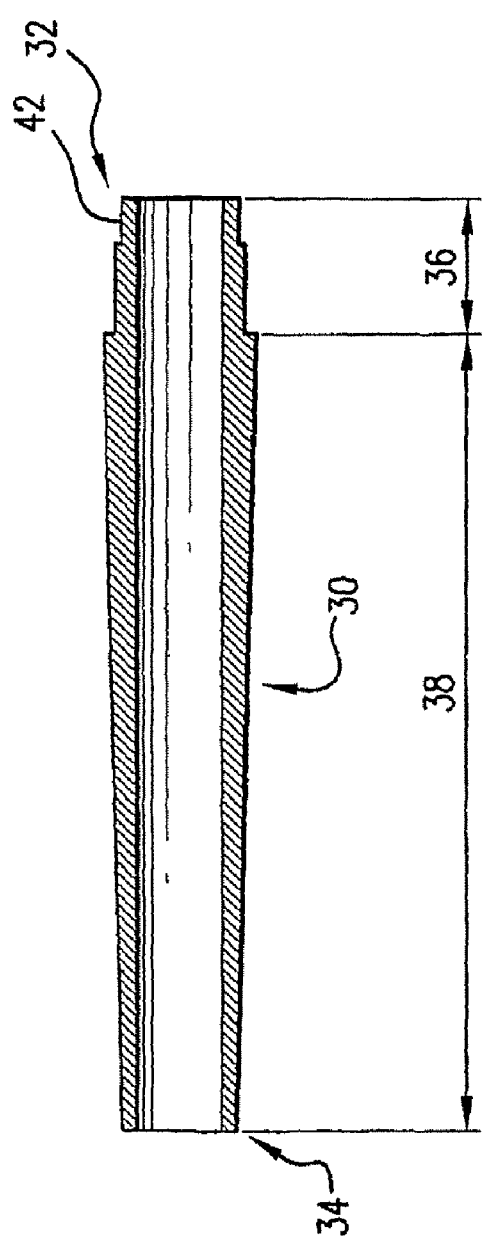
FIG. 4 is a partial cross sectional view of a distal tip portion of the device of FIG. 1.

Tip 30 is preferably, although not necessarily, formed as a separate piece from inner member 10. For purposes of illustration and not limitation and as depicted in FIG. 4, tip 30 has a proximal end 32, a distal end 34, and has a generally cylindrical shape with a substantially constant diameter section 36 and a distal tapered section 38. Tip 30 is molded from a relatively soft material, which may be softer than inner member 10 so as to reduce trauma to the vasculature of a patient. In accordance with a preferred embodiment of the invention, the tip is molded from a polyether block amide, sold under the trade name of PEBAX by Atofina Chemicals Inc. of Philadelphia, Pa. However, various other materials can be used for the tip as is known in the art. A preferred material is sold under the trade name of PEBAX 4033. It is further contemplated that the tip 30 may be made of a material that is harder and/or has greater stiffness than the inner member 10.

Preferably, distal end 34 of tip 30 is in longitudinal alignment with distal end 14 of inner member 10. Having inner member 10 traverse the entire length of tip 30 provides for a smooth surface for a guidewire (not shown) to move against inside lumen 18. Alternatively, if a discontinuity (not depicted) were present in lumen 18, such as if tip 30 extended beyond distal end 14 of inner member 10, a guidewire could collide with the discontinuity.

Suitable dimensions of tip 30 can include a length of about 0.5 inches, a distal external diameter of about 0.06 inches and a proximal outside diameter of about 0.08 inches, although actual dimensions will depend upon the intended application and the above dimensions should not be considered limiting in any manner and have been provided for exemplary purposes.

Tip 30 can be formed as a single piece with inner member 10 or made separately and then attached using any suitable technique, such as fusion bonding, laser welding/curing, UV bonding, adhesive or the like. Tip 30 is preferably mounted on the distal end 14 of the inner member 10 using an adhesive. In accordance with a preferred embodiment of the invention, the tip 30 is mounted on the distal end 14 of inner member. Next, an adhesive primer is applied to the joint created between proximal end 32 of tip 30 and inner member 10 and is permitted to dry. Preferably, the primer is selected so as to wick into the joint between the two components simply upon application. Next, an adhesive accelerator is applied to the joint and permitted to wick in and dry. An adhesive is then applied in a similar manner. Optionally, at this point, the inner member can be placed in a heated environment for a period of time sufficient to cure the adhesive. For example, the assembly can be placed into an oven for about 1-10 minutes at a temperature between about 50 and about 70 degrees centigrade. Preferably, the assembly is cured at about 57 degrees C. for about two minutes.

Preferred primer, accelerator and adhesive components include 7451 Loctite® accelerator, 7701 Loctite® primer and 4014 Loctite® adhesive from Loctite Corporation, although others can be used. For example, a UV cured adhesive may be utilized for assembly.

Figure 5:
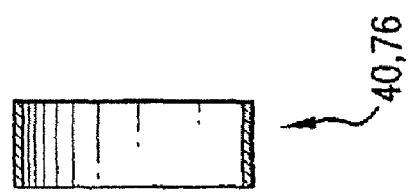
FIG. 5 is a partial cross sectional view of a radiopaque marker band of the device of FIG. 1.

For purposes of illustration and not limitation, as depicted in FIG. 5 herein, the tip 30 may further define a distal radiopaque portion 40. Distal radiopaque portion 40 may be a sleeve member that is formed separately from tip 30 and attached to the proximal reduced diameter portion 42, or may be formed integrally therewith. For example, radiopaque portion 40 can be formed by impregnating the polymeric material of tip 30 with radiopaque particulate such that the particulate become lodged in the polymeric structure. In this manner, it is possible for tip 30 to comprise a single integral piece. Alternatively, the radiopaque material can be applied as a coating or by other techniques as described below. Suitable materials that may be utilized to form the radiopaque portion 40 may include: gold, silver, nickel, stainless steel, tantalum, platinum, iridium, cobalt or similar materials or composites thereof which have desirable radiopaque features.

In accordance with an exemplary embodiment of the invention, distal radiopaque portion 40 is provided as a composite sleeve comprising platinum and iridium. Suitable dimensions of such a markerband include an outside diameter of about 0.065 inches, an internal diameter of about 0.062 inches, and a length of about 0.024 inches although the actual dimensions will depend on the intended application, wherein the dimensions above have been provided for exemplary purposes and should not be considered limiting in any manner. Such a markerband can be attached to tip 30 in a variety of ways. For example, Masterbond EP3HTMED Epoxy available from Masterbond, Inc. or Loctite 4014 adhesive can be used, although many other adhesives are appropriate and within the scope of the invention.

The delivery system in accordance with the invention further includes a bumper. The bumper is freely disposed on the inner member.

Figures 6A, 6B:
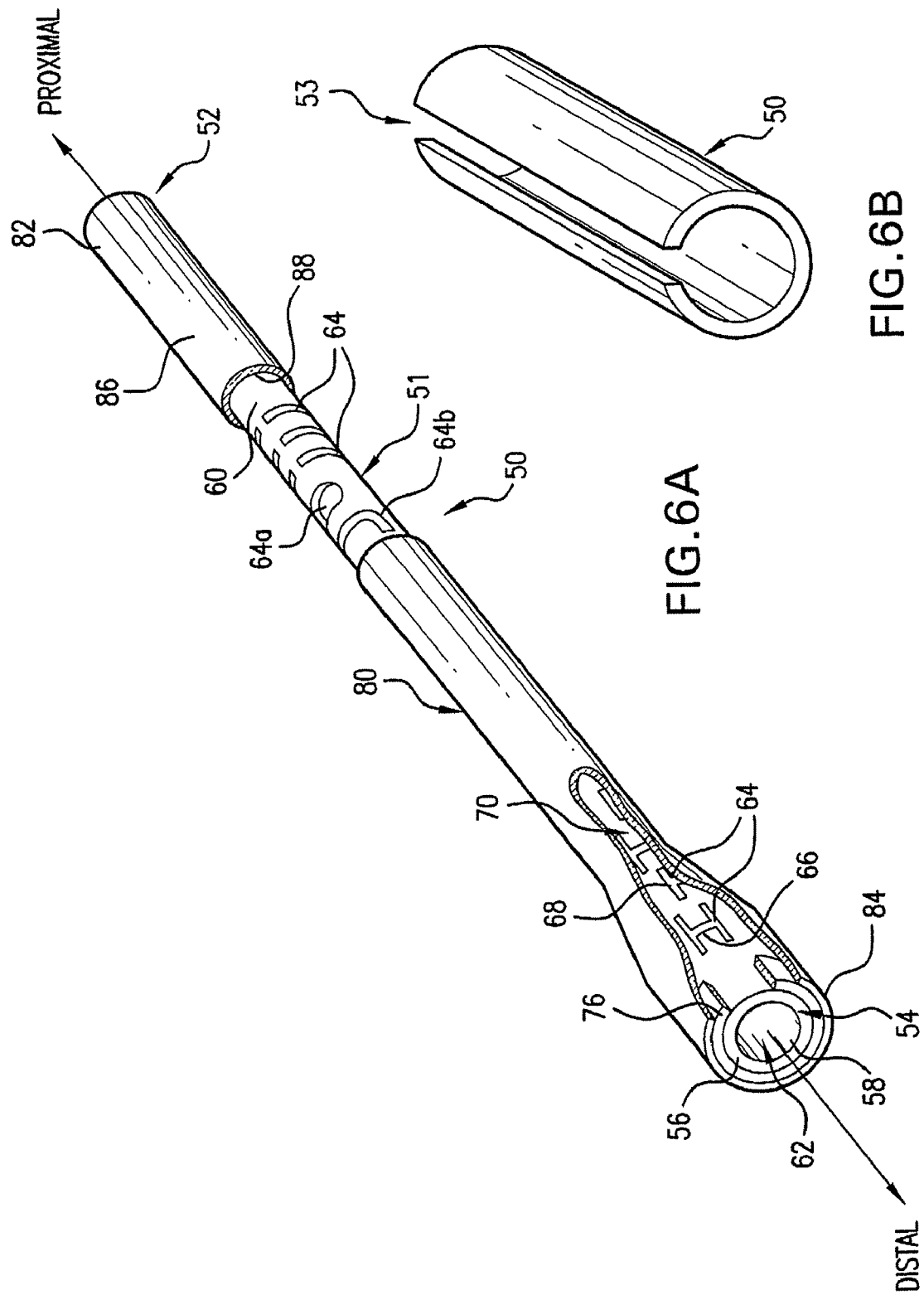
FIG. 6(a) is a fragmented perspective view of a bumper of the device of FIG. 1.
FIG. 6(b) is a perspective view of an alternative embodiment of a bumper of the device of FIG. 1.
Figure 7A:
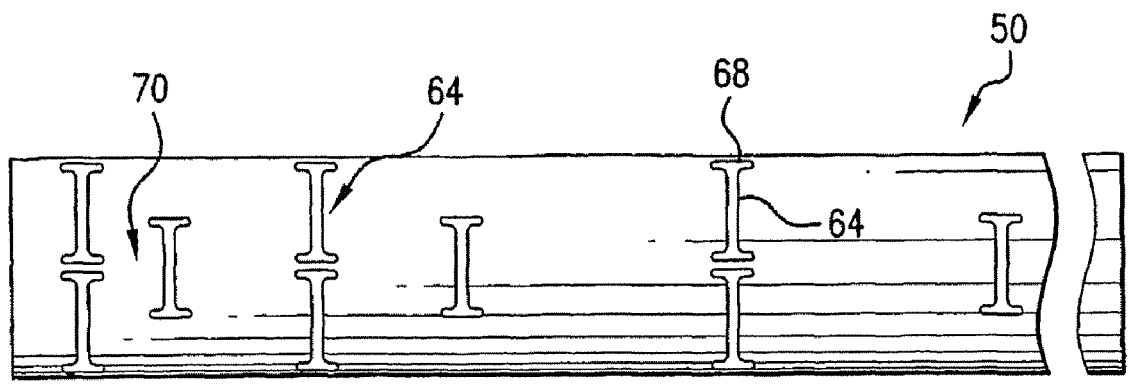
FIG. 7a is a plan view of a bumper of the device of FIG. 1.
Figure 7B:
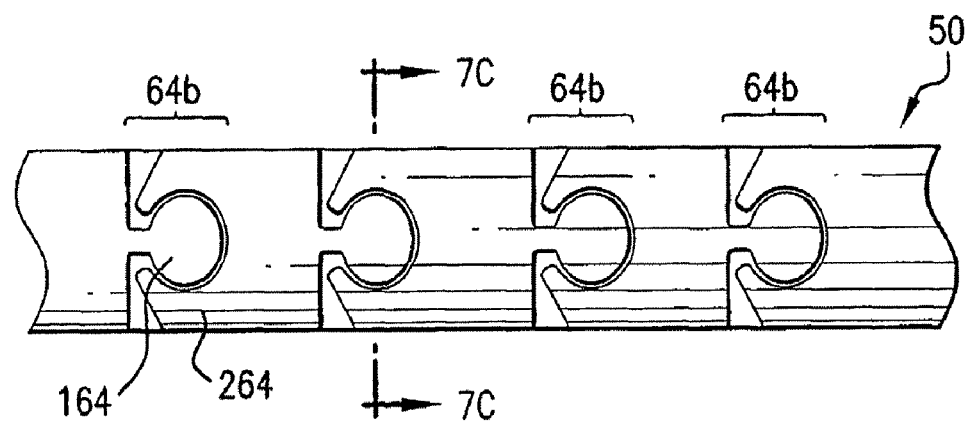
FIG. 7b is a plan view of an alternative embodiment of a bumper of the device in accordance with the present invention.

For purposes of illustration and not limitation, bumper 50 is schematically depicted in FIGS. 6-7b. Bumper 50 is generally a longitudinal sleeve member 51 including a proximal end 52 and a distal end 54, with a tubular wall 56 having inner surface 58 and outer surface 60 defining a lumen 62 therethrough. As embodied herein, lumen 62 is configured to permit passage of inner member 10 therethrough. Sleeve member 51 is preferably made from a metallic material such as stainless steel or nickel-titanium alloy, but can be made from any suitable material of sufficient compressive strength and flexibility, such as selected polymeric materials. Preferably, sleeve member 51 is made from 304V stainless steel tubing. Further still, the bumper may be constructed of multiple pieces that are assembled to form a longitudinal sleeve member as shown and described herein.

Bumper 50 may be further provided with a channel 53 as depicted in FIG. 6(b), such that bumper 50 is provided with a "C"-shaped cross-section. Channel 53 can be used to facilitate the flushing of a liquid such as saline solution and/or a beneficial agent to the patient. By providing channel 53, a larger flow channel is provided between inner member 10 and sheath 90, thereby permitting more fluid to be delivered to the patient with greater ease.

In further accordance with the present invention, the delivery system further includes at least one seat that is defined between the tip and the distal end of the bumper.

For purposes of illustration and not limitation, as embodied herein and as depicted in FIG. 1(b), a seat 116 is defined between proximal end 32 of tip 30 and the distal end 54 of bumper 50. Seat also occupies an annular space 118 defined between inner member 10 and sheath 90. Seat 116 is sized and shaped to receive a medical device 400 thereon, discussed in detail below. Seat 116, and hence medical device 400 will be exposed when a sheath, as will be described, is moved with respect to inner member 10 from a first sheath position substantially covering seat 116 as depicted in FIG. 1(b), to a second sheath position axially offset to expose seat 116.

Figure 15:
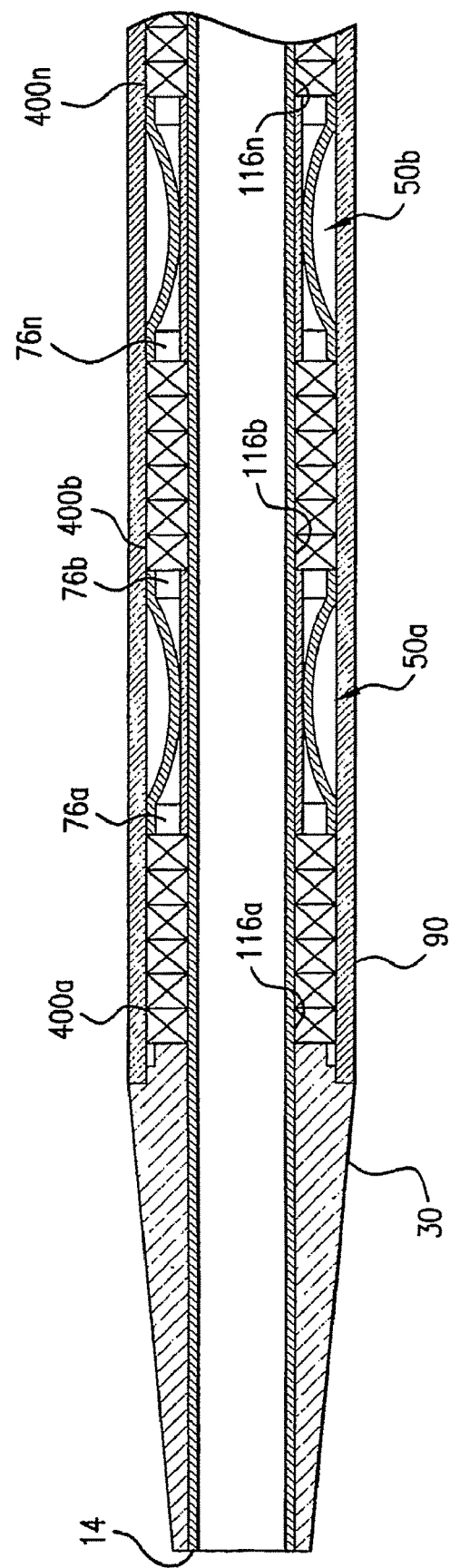
FIG. 15 is a partial cross-sectional view of an alternative embodiment of a delivery system in accordance with the present invention.

For purposes of illustration and not limitation, as depicted in FIG. 15, in further accordance with the invention, delivery system 300 can be provided with more than one seat 116 to permit delivery of more than one medical device 400. In accordance with this aspect of the invention, more than one bumper 50*a*-50*n* can be provided defining more than one seat 116*a*-116*n*, permitting delivery of more than one medical device 400*a*-400*n*. The multiple medical devices can be delivered in close proximity to one another, or further apart. If it is desired to deliver each of a plurality of medical devices to substantially displaced locations, it is possible to deliver a first medical device 400, and realign the distal end 98 of sheath 90 with tip 30, if desired, using the adjustment member 270 before moving delivery system 300 to a different location within the patient's vasculature system, as discussed in detail below. When more than one bumper 50 is provided, an intermediate bumper, such as 50*a* or 50*b*, can be provided with a radiopaque marker 76*a*-*n* at each end to help aid in visualization and delivery of the medical device 400 and/or placement of the delivery system 300 within a patient's vasculature system.

An additional restraining device (not shown) can also be provided to prevent axial movement and/or radial expansion of medical device 400. Such a device can include a membrane or resilient clip. It would also be possible to provide seat 116 with a number of radial protrusions affixed thereto to prevent axial displacement of medical device 400 during delivery thereof. Further still, it is contemplated that after disposing the medical device 400 within seat 116, a retaining agent may then be disposed thereupon to aid in retaining the medical device 400 within the seat 116. The retaining agent may be configured to be dissolvable upon contact with a fluid such as saline, blood or other biocompatible fluid.

Referring now to FIG. 9B, there is shown an alternative embodiment of the seat 116 of the present invention, wherein a stent retention feature 31 is shown formed on the proximal end of the tip 30. A similar conically configured feature, or the like, is be formed on the distal end of the bumper 54. The retention feature includes a recess 31 to receive and radially constrain a distal end of a stent disposed in the seat 116. The retention feature 31 is formed having first and second angled surfaces and a generally flat section joining the two angled surfaces. In use, the ends of the stent 405 are received by the first and second angled surfaces, thereby compressing the ends of the stent and forming a space between the outer surface of the stent 400 and the inner surface of the sheath 90 as shown. The space formed between the stent and the sheath reduces friction forces between the stent and sheath during retraction of the sheath for delivery of the stent as described in detail herein.

Another embodiment of the stent retention feature includes a thin rigid member constraint attached to the distal end of the bumper. As embodied herein and shown in FIG. 9C, the constraints can be configured as two rigid members 600 extending distally from the distal end of the bumper 54. The rigid member 600 is configured to receive an end of the stent. Yet another embodiment is shown in FIG. 9D where the distal end of the bumper 54 is shaped to receive an end of the stent. It shall be understood that although the retention feature has been described with regard to specific geometric configurations these should not be considered limiting in any manner, and that other geometric configurations may be utilized to achieve the desired results described herein.

For example and not limitation, the delivery system in accordance with the present invention can be used for delivery of a self-expanding stent having eyelets disposed on the ends of the stent. If desired, the delivery system can include a retention mechanism configured to receive the eyelets of the stent in a contracted configuration to reduce delivery force.

In another aspect of the invention, as shown in FIGS. 7D and 7E, the inner member 10 is a tubular member having a proximal end, a distal end, and a length therebetween. The sleeve member of the bumper is formed of a flexible metallic element 720 disposed along at least a portion of the length of the inner member 10. As embodied herein, the bumper further includes an outer layer 706 over at least a portion of the flexible metallic element 720. The bumper also define a first portion 714 along the length of the inner member having a first diameter and a second portion 712 along the length of the inner member having a second diameter. The first diameter is greater than the second diameter.

As embodied in FIG. 7D, The first diameter is defined by the inner member 10 and bumper 50 combined, and the second diameter is defined by the inner member 10. The second diameter defines the seat 716. As shown in FIG. 7B, the inner member 10 defines a guidewire lumen along a length thereof. In a preferred embodiment, the inner member is formed of a lubricious material. The inner member 10 can be secured to the bumper.

As embodied herein, the outer layer 706 is formed from a polymeric material. As shown in FIGS. 7D and 7E, the flexible metallic element is a braid or coil element.

In another embodiment of the invention, the bumper 50 is freely disposed on the inner member 10.

In further accordance with the invention, bumper 50 is configured to move freely on inner member 10 with no points of fixation therebetween. Distal end 54 of bumper 50 abuts medical device 400. The proximal end 52 of bumper may optionally abut a hypotube 250 (See FIG. 2). By permitting bumper 50 to move freely, it is possible to permit the longitudinal positions of the various components (e.g., tip 30, medical device 400, bumper 50, hypotube 250) of delivery system 300 to be adjusted relative to one another after receipt by the physician. Thus, when the delivery system is assembled with a medical device 400 thereon, it is possible to build up a desired longitudinal tolerance between tip 30, medical device 400, bumper 50, and any other components that are disposed on inner member 10.

For purposes of illustration and not limitation, as embodied herein, tubular wall 56 of bumper 50 preferably has one or more perforations 64 defined therein. As shown in FIG. 6(*a*), perforations 64 generally are oriented circumferentially about tubular wall 56. Preferably, in accordance with this exemplary embodiment of the invention, the perforations 64 are disposed circumferentially about wall 56 in pairs so as to define hinge points 70 therebetween (See FIG. 7). As depicted, each perforation 64 subtends an angle of less than 180 degrees of the circumference of cylindrical wall 56. However, a single perforation subtending an angle greater than 180 degrees is also within the scope of the invention. Perforations 64 can be formed by laser discharge, milling, etching or any other suitable techniques.

Collectively, perforations 64 are preferably sized and shaped, and spaced from one another to modify the flexural characteristics of bumper 50 in a predetermined manner without altering the compressibility of bumper 50. For example, alternating pairs of perforations 64 can be rotated with respect to each other by a predetermined angle, such as 90 degrees as depicted in FIG. 6(*a*). In this manner, it is possible to provide for enhanced flexure of bumper 50 in two directions that are substantially perpendicular to one another. Similarly, the longitudinal spacing between perforations can be varied to provide for varying rigidity along the length of bumper 50. Likewise, the circumferential placement of perforations 64 about sleeve 51 can be varied to impart desired bending characteristics to bumper 50.

In accordance with an exemplary embodiment, for purpose of illustration and not limitation, sleeve member 51 has a total length of about 30 inches and pairs of perforations are spaced from each other longitudinally by about 0.1 inches on center in a more distal portion of sleeve member 51, and by about 0.2 inches on center in a more proximal portion of sleeve member 51. Additional spacings between perforations along the length of the sleeve member 51 may be implemented, if desired, to vary flexural characteristics gradually, or in a step like fashion.

There are many ways in which the perforations 64 can be shaped and arranged in accordance with the invention. For example, the perforations can be varied in size and/or in longitudinal spacing to create regions of greater or lesser axial flexibility. Furthermore, alternating pairs of perforations 64 need not be alternated merely by rotating them 90 degrees. Any pattern of rotation to create a desired bending characteristic can be achieved.

Moreover, the perforations do not need to be circumferentially aligned slit shapes. For example, and in accordance with an alternate embodiment of the invention as depicted in FIGS. 6-7a, perforations 64 may include longitudinal components, such as an I-shape. In accordance with this aspect of the invention, perforations 64 include a circumferential component 66 and a longitudinal component 68. When arranged as shown in FIG. 7a, perforations 64 define hinge points 70 therebetween.

A variety of other shapes and arrangements are possible for perforations 64. For example, as depicted in FIG. 6, curved perforations can also be used. In accordance with this aspect of the invention, the perforations can be ellipsoidal in shape (64a) or could take the form of a curved slot (64b).

Figure 7C:
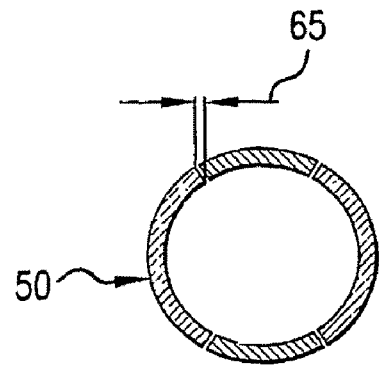
FIG. 7c is a cross-sectional view of the alternative embodiment of the bumper taken about line 7c of FIG. 7b.

Referring now to FIGS. 7b and 7c, there is shown an alternative embodiment of a bumper 50 in accordance with the present invention wherein the bumper 50 includes a plurality of articulating joints 64b instead of slots 64 as shown and described above with reference to FIGS. 6-7a. The articulating joints 64b as shown in FIG. 7b and 7c, are configured to have male 164 and female 264 components, wherein the male component 164 is configured to be received by the female component 264. The male and female components 164, 264 are retained by one another by an overlap of the wall thickness at the rounded portion of the joint between the male and female components as shown in FIG. 7c, and referenced by callout 65. The overlap can be described as being the relation of the tube circumference to the diameter of the circular diameter of the male component. A preferred relation between the diameter of the male component and the circumference of the tube is about 0.25. The connection between the male and female components may gain further support by overcoating or covering the plurality of articulating joints with a covering such as heat shrink tubing or the like.

There are many ways in which the articulating joints 64b can be shaped and arranged in accordance with the invention. For example, the articulating joints can be varied in size and/or in longitudinal spacing to create regions of greater or lesser axial flexibility. Furthermore, alternating pairs of articulating joints 64b need not be alternated merely by rotating them 90 degrees. Any pattern of rotation to create a desired bending characteristic can be achieved.

In yet another alternative embodiment, the bumper 50 may be formed of one or more coil assemblies. It is contemplated that two coil assemblies can be utilized to form the bumper 50, wherein an inner coil is wound having a specific pitch and the outer coil is wound having a specific pitch, wherein the coils' pitches define flexible properties of the bumper 50. The flexibility of the bumper 50 may be further tuned or adjusted by varying the thickness of the material from which the coil assemblies are constructed of.

Ordinarily, if perforations 64 are provided, a physician must be careful to ensure that all air is purged from delivery system 300 before it is introduced into a patient, since introducing air into a patient's blood stream can have dire consequences. Thus, in accordance with an additional aspect of the invention, perforations 64 are filled in with a filling material that is flexible relative to the material that sleeve 51 is made from. Examples of suitable materials include, but are not limited to polymeric materials. Even more preferably, an elastomeric material can be used. By using a material that is flexible, the flexibility characteristics imparted to sleeve member 51 by perforations 64 are not lost. The filling material can be molded over sleeve 51, for example, in an overmolding process.

The filling material thus fills in the voids created by perforations 64 that would otherwise be filled by air. By filling in perforations 64, the air is displaced, so air cannot become trapped in perforations 64 when a physician flushes device 300 in preparation for a procedure.

Moreover, using a filling material can provide additional advantages. The filling material can include a beneficial agent. Such a beneficial agent can be delivered to a location inside of a patient, for example, by exposing perforations 64 containing the beneficial agent. If so configured, the filling material 64 will dissolve, thereby releasing the beneficial agent into the patient's bloodstream. Optionally, a release agent can be flushed through device 300 such that, upon contacting the filling material, causes the beneficial agent to be released into the patient's bloodstream. Such a release agent can, for example, be directed through flush port 240 (described in detail below) and subsequently through channel 53 defined in bumper 50.

In accordance with another aspect of the invention, as embodied herein and as depicted in FIGS. 5-6, a proximal radiopaque portion 76 can be provided. As embodied herein, proximal radiopaque portion 76 is provided in the form of a markerband, similar to distal radiopaque portion 40. Proximal radiopaque portion 76 is disposed about, and preferably attached to, distal end 54 of bumper 50. Attachment is preferably provided via adhesive bond. Suitable adhesives include, for example Loctite™ 4014 adhesive obtainable from Loctite Corp. Attachment may be accomplished in other manners as well. For example, where proximal radiopaque portion 76 is provided as a metallic member, it can be attached to tubular wall 56 of bumper 50 by way of swaging, soldering, press fitting or brazing. If proximal radiopaque portion 76 is provided as a polymeric member containing radiopaque particulate material, it can be molded over sleeve 56. Alternatively, a radiopaque dye can be applied directly to the sleeve member surface.

As with distal radiopaque portion 40, proximal radiopaque portion 76 can take any one of a number of forms as described in detail above. In accordance with an alternative embodiment of the invention, proximal radiopaque portion 76 can be provided as a coating applied to bumper 50. For example, distal end 54 of bumper 50 can be coated with a radiopaque material such as silver, tantalum, gold, tungsten, platinum, iridium and the like or any composites thereof. Similarly, distal end 54 can be dipped into a suitable radiopaque coating such as a polymer coating, having a radiopaque material entrained therein, or such a coating could be applied to bumper 50 by other methods including extrusion, spraying or any other suitable method.

In accordance with an additional aspect of the invention, as depicted in FIG. 6(a), a covering member 80 is be provided for bumper 50. As depicted herein, covering member 80 has a proximal end 82, a distal end 84, an exterior surface 86 and an interior surface 88. Preferably, covering member 80 is heat shrinkable tubing or the like, although alternative films of membranes can be used. The covering can be disposed about the sleeve member.

Covering member 80 is preferably applied to sleeve 51 after affixing proximal radiopaque portion 76 thereto. With reference to the heat shrink embodiment of FIG. 6(*a*), covering member 80 is preferably applied to sleeve 51 in the following manner. First, a suitable length of heat shrinkable tubing, preferably exceeding bumper 50 in length, is cut and fit over sleeve 51, including proximal radiopaque portion 76 (if provided). Next, the covering member 80 is stretched from either end into tension. The assembly including sleeve 51, proximal radiopaque portion 76 and covering member 80 is subsequently brought in communication with a heat source sufficient to cause covering member 80 to shrink around sleeve 51. Once the heating step is completed, excess covering material is trimmed from bumper 50.

Covering member 80 can take on a variety of forms. Although heat shrinkable tubing is depicted herein, using heat shrinkable tubing is not necessary. In accordance with an alternative embodiment of the invention, covering member 80 can be extruded over bumper 50. Alternatively, covering member 80 can take the form of a tape material wrapped around bumper 50, and, if necessary, melted together to form a covering. In lieu of providing a separate radiopaque marker, distal end 84 of covering member 80 can be impregnated with radiopaque material to form proximal radiopaque portion 76, described in detail above. Suitable materials that can be used to form covering member 80 include, but are not limited to heat shrinkable polymeric materials. It is further contemplated that the covering member 80 may be disposed upon the bumper 50 through a dip coating, spray coating, extrusion, or other similar manufacturing processes. The covering member 80 may impart mechanical properties, which are desirable to the functionality of the device; for example, the covering member may include a friction reducing coating, a beneficial agent or other similar biocompatible coatings. Further still, the covering member may be constructed of more than one material along the length of the bumper.

The delivery system in accordance with the present invention further includes a sheath disposed about the inner member, wherein the sheath has a proximal end and a distal end. The sheath is movable between a first sheath position substantially covering the seat, and a second sheath position axially offset with respect to the first sheath position to expose the seat.

For purposes of illustration and not limitation, as embodied herein, FIGS. 8(*a*)-8(*b*), show a representative sheath 90 having a proximal portion 92 terminating in proximal end 94, a distal portion 96 terminating in distal end 98, an outer surface 100 and an inner surface 102. Sheath 90 can extend over the entire length of inner member 10 or only a portion thereof. Sheath 90 must be of a sufficient length to capture medical device 400 in seat 116. Sheath 90 can be a single piece construction, or can be made from multiple pieces of material.

Figure 8A:
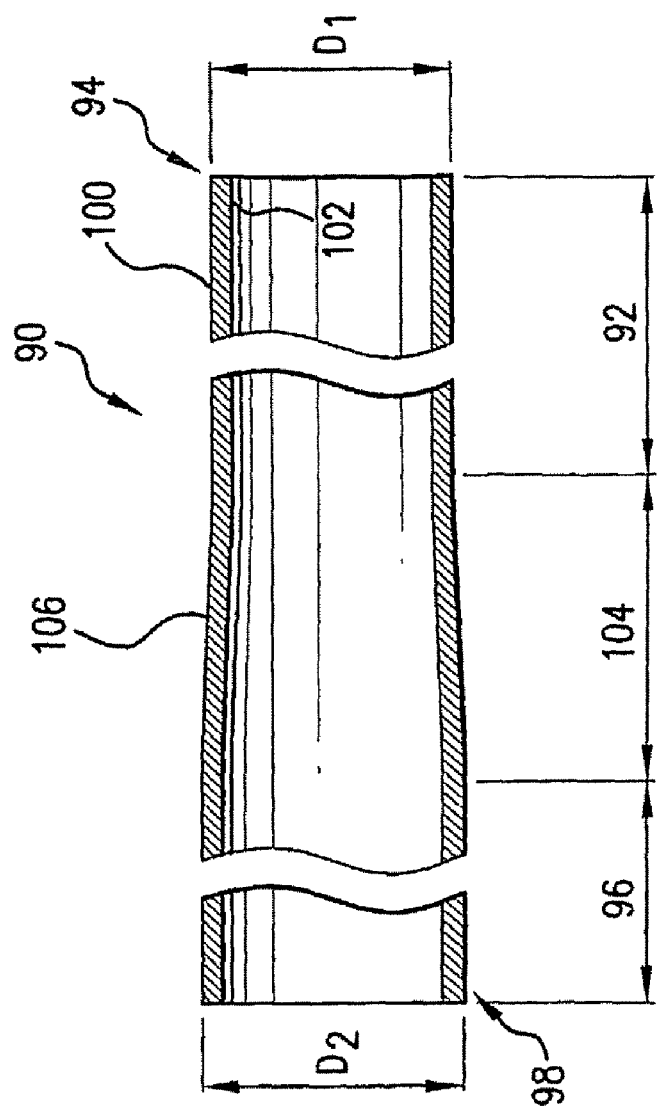
FIGS. 8(a)-8(d) are a cross-sectional view, plan view and cutaway views of a sheath of the device of FIG. 1.
Figure 8B:
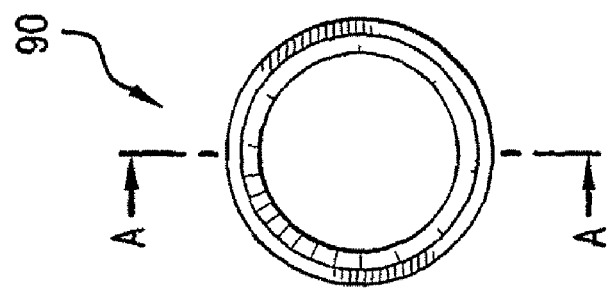

As shown in FIG. 8F, the sheath 90 is formed having a tapered profile. The sheath includes an inner surface 102 and an outer surface 100 that define a wall thickness. In a preferred embodiment, the wall thickness of the sheath is greater at the distal end than the proximal end. Wherein as shown in FIG. 8F, the inner surface 102 of the sheath 90 would be contact with the stent 400 wherein the inner wall of the sheath proximal the seat 116 would be formed having a decreasing wall thickness proximal toward the handle portion 120 of the device. By reducing the wall thickness of the sheath proximal to the stent, frictional drag can be reduced during deployment of the stent by reducing and/or eliminating contact of the inner surface 102 of the sheath 90 with the bumper 50.

Figure 8D:
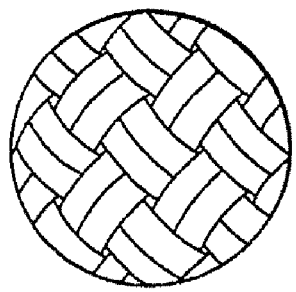
Figure 8E:
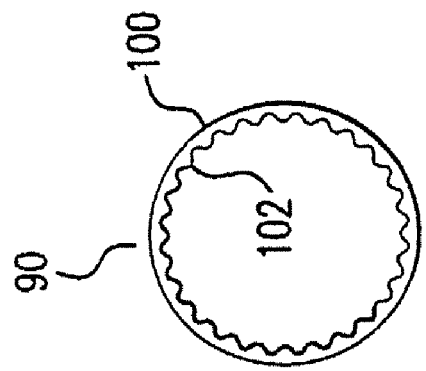
FIG. 8E is a cross-sectional view of an alternative embodiment of a sheath in accordance with the present invention.

In yet another sheath embodiment, shown in FIG. 8E, wherein there is shown an exemplary cross-sectional view of an alternative sheath design in accordance with the present invention. As shown in FIG. 8E, the inner wall 102 of the sheath 90 is formed having a non-uniform surface. As shown in FIG. 8E, the inner wall of the sheath is formed having a repeating pattern formed therein, the pattern forming a sinusoidal pattern about the inner circumference of the sheath 90. By forming the inner wall 102 in the manner shown in FIG. 8E, frictional forces between the inner wall 102 of the sheath 90 and the outer surface of the bumper 50 and the stent 400 can be reduced by forming points of contact between the two surfaces instead of a continuous surface contact between the two surfaces. The multiple contact points reduce friction between the sheath and the stent 400 as well as the bumper 50, thereby requiring less force to retract the sheath during use. The sheath illustrated in FIG. 8E can be fabricated as a unitary member or fabricated of more than one element.

In accordance with the invention, it is possible to provide sheath 90 with varied stiffness (i.e., durometer) along its length. This may be accomplished in a variety of ways. For example, proximal portion 92 of sheath 90 embodied herein can include a first material and distal portion 96 of sheath 90 includes a second, different material at its distal end 98. In accordance with the invention, the sheath may also define an intermediate region 104 wherein the first material is blended with the second material. For example, the first material can be a first polymer material and the second material can be a second, different polymer material. In accordance with an exemplary embodiment of the invention, distal portion 96 of the sheath has a length of about 4 inches, and sheath 90 has a total length of about 50 inches. It is understood that the dimensions of sheath 90 will depend on the intended application.

The second polymer material incorporated into distal portion 96 of sheath 90 can be less stiff than the first polymer material 94 in proximal portion 92 of sheath 90.

For example, the first polymer material can include NYLON 12 and the second polymer material can include NYLON 68D. Other polymer materials however, may be used in lieu of or in combination with the above-described materials. For example, a block copolymer material such as Pebax 7233 can be used.

Alternatively, other materials such as polyvinylchloride (PVC) or polyurethanes can be used.

Variation in stiffness can be predetermined by blending the materials in varying proportions along the length of sheath 90 such that the majority of material at the proximal end 94 of sheath 90 is NYLON 12 and the majority of material at distal end 98 of sheath 90 is NYLON 68. It is also be within the scope of the invention to vary the rigidity of sheath 90 by varying the diameter along the sheath.

Additionally or alternatively, the sheath 90 can define a first external diameter D1 at its proximal end 94, and a second, different external diameter D2 at its distal 30 end 98. Preferably, the first diameter is smaller than the second diameter. For example, and in accordance with a representative embodiment of the invention, the sheath 90 can have a D1 of about 5.5 French and a D2 of about 6.0 French, although these dimensions can vary depending on the intended application. In accordance with this aspect of the invention and as depicted in FIG. 8(*a*), a step 106 is provided to allow for the change in diameter between the proximal end 94 and distal end 98 of sheath 90. Step 106 allows for the change in diameter to occur over a longer or shorter distance along sheath 90, depending on the application. Alternatively, a more gradual taper can be provided if desired.

In accordance with another aspect of the invention, the sheath can include an outer layer and an inner layer.

Figure 8C:
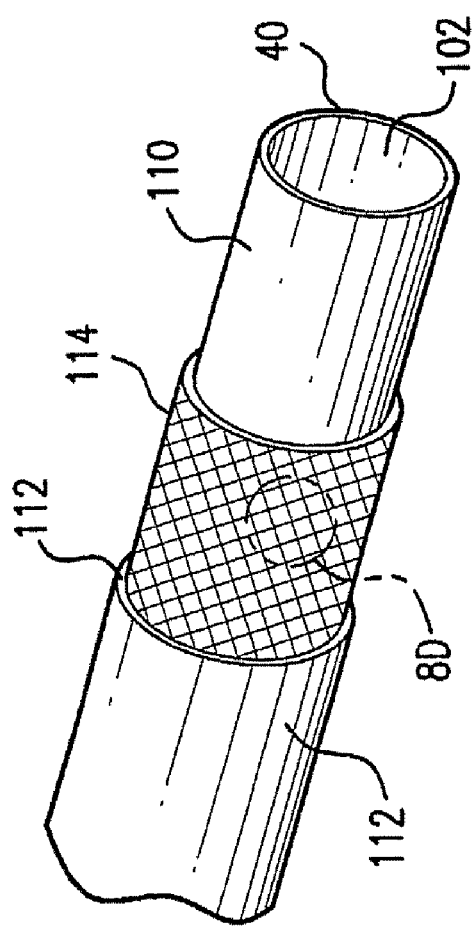

For purposes of illustration and not limitation, as embodied herein and as depicted in FIG. 8(c), sheath 90 can be provided with an inner layer 110 attached to or formed with an outer layer 112. Preferably, inner layer or liner 110 includes a lubricious material to facilitate the sliding of sheath 90 in a proximal direction when the medical device 400 is deployed. For example, different types of polymers such as PTFE or high-density polyethylene (HDPE) can be used for the inner layer 110. Additionally, other lubricious polymers can be used. The outer layer 112 preferably provides sufficient strength to capture a medical device 400 therein, as well as allow movement between the first position and the second position. The multiple layers can be formed separately and adhered or bonded together or co-extruded as a single member.

In another embodiment as depicted in FIG. 8G, the inner layer can be formed as a liner 110 with a varied wall thickness. The liner has an inner surface 800 and an outer surface 802, thereby defining a wall thickness. The 30 wall thickness has a greater width at the distal end than the proximal end. The outer surface 802 of the liner is secured to the inner surface 802 of the sheath 90. The inner surface 802 of the liner may be lubricious, as described above.

In further accordance with the invention and as depicted in FIGS. 8(c) and 8(d), sheath 90 can include a reinforcing layer 114 disposed between the outer layer 112 and the inner layer 110. Preferably, the reinforcing layer 114 includes braided material. For example, the reinforcing layer 114 can be provided in the form of a braided stainless steel tube or sheet (See FIG. 8(c)). Preferably, the braid includes flattened filaments, as opposed to having filaments with a round cross-section. Although a metallic braided material such as that depicted in FIG. 8(d) is preferred, it is not necessary. It is also possible to provide a tube including woven fabric or appropriately oriented filaments, such as carbon fibers encased in a polymeric matrix. Likewise, such reinforcing fibers could additionally or alternatively be incorporated into inner layer 110 and/or outer layer 112 during the manufacturing process. The reinforcing layer 114 need not be present through the entire length of the sheath. For example, it is possible for reinforcing layer to be provided along the proximal portion 92 of sheath 90 only, or some greater or lesser portion.

In accordance with an exemplary embodiment of the invention, sheath 90 has a wall thickness of about 6.0 mil, wherein inner layer 110 and reinforcing layer 114 have a thickness of about 2.0 mil, and outer layer 112 has a thickness of about 4.0 mil. Wherein the dimensions above are provided as examples and should not be considered limiting in any manner.

When sheath 90 is provided with an inner layer 110, outer layer 112 and a reinforcing layer 114 sheath 90 is preferably formed in the following manner. First, inner layer 110 is formed through a tubular extrusion process, and disposed about a forming mandrel (not shown). The forming mandrel preferably has a shape that corresponds to the desired shape of the inside of the sheath 90. Next, reinforcing layer 114, preferably provided in the form of a stainless steel raid material, is positioned over a predetermined length of inner layer, preferably leaving a distal portion of the inner layer 110 uncovered by reinforcing material. Next, the outer layer 112 is extruded and positioned over the reinforcing layer 114. Preferably, outer layer 112 is provided in the form of two separate tubular members that are overlapped slightly at their ends over reinforcing layer 114. Each portion of outer layer 112 can be a different material selected to provide a different durometer as described above. The two portions of outer layer 112 can overlap by an amount such as about 0.1 inches. Next, a sleeve of heat shrinkable material is positioned over the entire sheath assembly. Finally, heat is applied to the assembly. When heat is applied, the heat shrinkable tubing shrinks, and causes inner layer 110 to fuse with outer layer 112, trapping reinforcing layer 114 therebetween. The heating process also causes inner layer 110 to conform to the shape of the forming mandrel. Thus, if it is desired to have a sheath 90 with a varied and/or stepped diameter as described above with regard to FIG. 6B, the mandrel can be formed accordingly. After the assembly cools, the heat shrinkable tubing is cut away, leaving behind sheath 90.

In further accordance with the invention, the delivery system includes a handle connected to the proximal end of the inner member. The handle is used to manipulate the delivery system through a patient's lumen and to deploy the delivery system to deliver the medical device.

For purposes of illustration and not limitation, as embodied herein and as depicted in FIGS. 1 and 2, handle 120 is connected directly to inner member 110 if desired or necessary. However, an indirect connection through an intermediate coupling can be provided, as described in detail below. Handle 120 has a proximal end 122, a distal end 124 and an external gripping surface 126. Preferably, handle 120 is also provided with an actuator 130 to move sheath 90 from the first sheath position to the second sheath position, as discussed in detail below. When the delivery system 300 includes an internal actuator mechanism 130 as depicted in FIGS. 1-2, handle 120 can further include a nose piece 210, as discussed below.

Handle 120 is preferably formed of a plastic material, although other suitable materials can be used. For example, handle 120 can be made from ABS plastic and/or polycarbonate and may include fiberglass fiber reinforcement. optionally, gripping surface 126 may be enhanced by applying a softer material thereto to enhance gripping. For example, a coating of rubber (not shown) or other similar elastic material can be used to enhance gripping and thereby make it easier for a physician to traverse the patient's vasculature using the delivery system.

In further accordance with the invention, an actuator can also be provided. The actuator is disposed on the handle and is configured to move the sheath with respect to the inner member along its longitudinal axis 15 (See FIG. 1(a)) from the first sheath position to the second sheath position, thus uncovering the seat to permit a medical device captured or contained therein to be deployed.

As embodied herein, and in accordance with one aspect of the invention, actuator 130 can include a push-pull configuration as depicted in FIG. 10. In accordance with this aspect of the invention, proximal end 94 of sheath 90 is attached to actuator 130, and the proximal end 12 of inner member 10 is attached to handle 120. In accordance with this embodiment of the invention, Sheath 90 can be moved from the first sheath position to the second sheath position by moving actuator 130 proximally, toward handle 120. As actuator 130 is moved with respect to handle 120 seat 116 is uncovered, thereby permitting medical device 400 to be deployed. The ratio of sheath movement to actuator movement can be greater than one to one.

This embodiment of the invention presents the advantage that the position of inner member 10 and hence, the position of medical device 400, remains stationary in the patient's vasculature as sheath 90 is moved proximally. This permits precise placement of the medical device 400.

Moreover, actuator 130 can take on a variety of different forms. For purposes of illustration and not limitation, in accordance with another embodiment of the invention and as depicted in FIG. 1(a), the actuator 130 can include a rotatable member and shuttle assembly to translate rotational movement of the rotatable member into linear movement of the sheath.

Figure 22A:
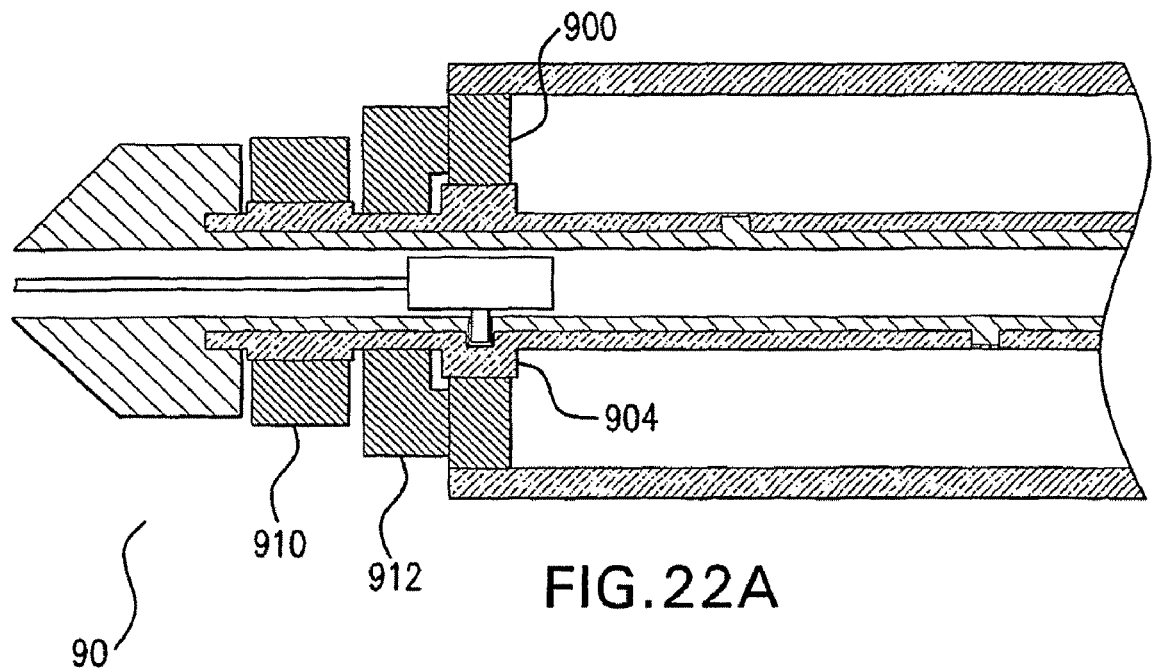
FIGS. 22a through 22b are partial views of an alternative embodiment of a sheath retraction mechanism in accordance with the present invention.
Figure 22B:
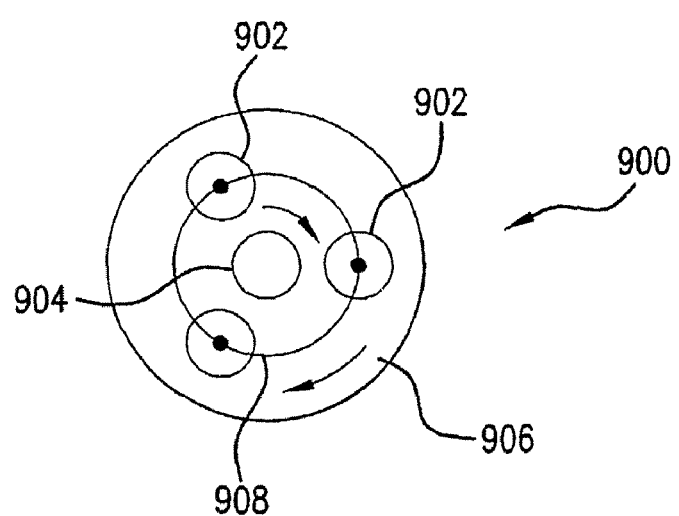

In accordance with another embodiment, as shown in FIGS. 22a and 22b, the actuator includes a planetary gear train 900 to longitudinally retract the sheath. The planetary gear train, as known in the art, generally includes at least one planetary gear 902 attached to a carrier plate 906 and operationally engaged to a ring gear 908, and a sun gear 904 operationally engaged to each of the at least one planetary gear 902. Each of the gears include teeth along their outer surfaces. A gear ratio of this embodiment can be 3:1 or 2:1 or any other desired ratio. The sun gear 904 is operationally attached to a coarse adjust element 910, such as a thumbscrew, and each of the at least first and second planetary gears 902 is operationally attached to a fine adjust element 912. As embodied herein, three planetary gears are provided.

The planetary gear train (or set) 900 provides a mechanical advantage to the user. The gear ratio provides this advantage. The ratio depends on the number of teeth on the ring gear 908 compared to the number of teeth on the sun gear 904. For example, if there are 60 teeth on the ring gear and 30 teeth on the sun gear, the gear ratio is one plus 60 divided by 30 (which is 3) or 3:1. The planetary gear train 900 allows for multiple deployment speeds for the stent. The gear train 900 may be located either in the front or the back of the handle.

A first gear provides a first deployment rate for movement of the sheath and a second gear provides a second deployment rate for the movement of the sheath.

In accordance with this aspect of the invention, sheath 90 can be advanced proximally with respect to inner member 10 to uncover seat 116.

The proximal end 94 of sheath 90 is preferably attached, either directly or indirectly, to a shuttle 140, wherein shuttle 140 is configured to travel in a shuttle guide 160. As embodied herein, shuttle 140 has a proximal end 142, a distal end 144, an external surface 146 and a lumen 148 defined therethrough. Lumen 148 has a proximal section 150 and an enlarged distal section 152. Distal section 152 of lumen 148 is sized to receive proximal end 94 of sheath 90. Sheath 90 is preferably attached to shuttle 140 by way of adhesive bonding, although alternative attachment techniques can be used such as fusion bond or force fit. When an adhesive bond is used, glue ports 151 are preferably provided for injecting an adhesive material, such as Loctite 4014, into section 152. Shuttle 140 is further provided with a proximal groove 154 and a distal groove 156 (See FIG. 2), each of which are configured to receive an o-ring 158. O-rings 158 are configured to prevent flushing liquid from flowing into handle 120 as discussed below in the discussion of flush port 240. An additional inner seal 153 (see FIG. 1(d)) is provided in proximal section 150 of lumen 148 proximal to flush port 149 to seal between shuttle 140 and hypotube 250.

Shuttle 140 is preferably made of a moldable polymeric material with reinforcement fibers. For example, shuttle 140 can be made from a mixture of nylon 66 and fiberglass, although other suitable materials can be used.

Preferably, shuttle 140 is provided with rails 145 formed thereon (not shown) that are configured to ride in longitudinal slots 162 in a shuttle guide 160 to permit axial movement but not rotational movement of the shuttle 140. Shuttle 140 is further provided with a protuberance 147 thereon. Protuberance 147 is configured to mate with a helical guide groove 176 in thumbscrew 170 (See FIG. 2). Thumbscrew 170 has a proximal end 172, a distal end 174, and an exterior surface 178. Thumbscrew 170 is attached at its distal end 174 to proximal end 182 of knob 180. Attachment is preferably achieved by adhesive connection, but may also be achieved by way of bonding, welding, snap-fit, force-fit or threaded connection. Knob 180 and thumbscrew 170 thus cooperate to form a thumbscrew assembly 188 (See FIG. 1(a)), and are configured to rotate about shuttle guide 160. Thumbscrew 170 and knob 180 are preferably made from a polymeric material such as ABS plastic via injection molding.

In operation, when a user rotates knob 180 and thumbscrew 170 about the longitudinal axis of the delivery system 300, protuberance 147, and hence, shuttle 140 with sheath 90 attached thereto is advanced in a proximal direction, withdrawing the distal end 98 of the sheath and exposing seat 116. It is further contemplated that the helical groove 176 may be formed having more than one thread pitch. For example, when the sheath is initially being retracted, it may be desirable to move the sheath a greater amount for each rotation of the thumbscrew, this prevents the medical device from "jumping" during deployment and enables more precise placement of the medical device within the patient's vasculature. After initial movement of the sheath, the thread pitch may be changed to slow the movement of the sheath.

Figure 11:
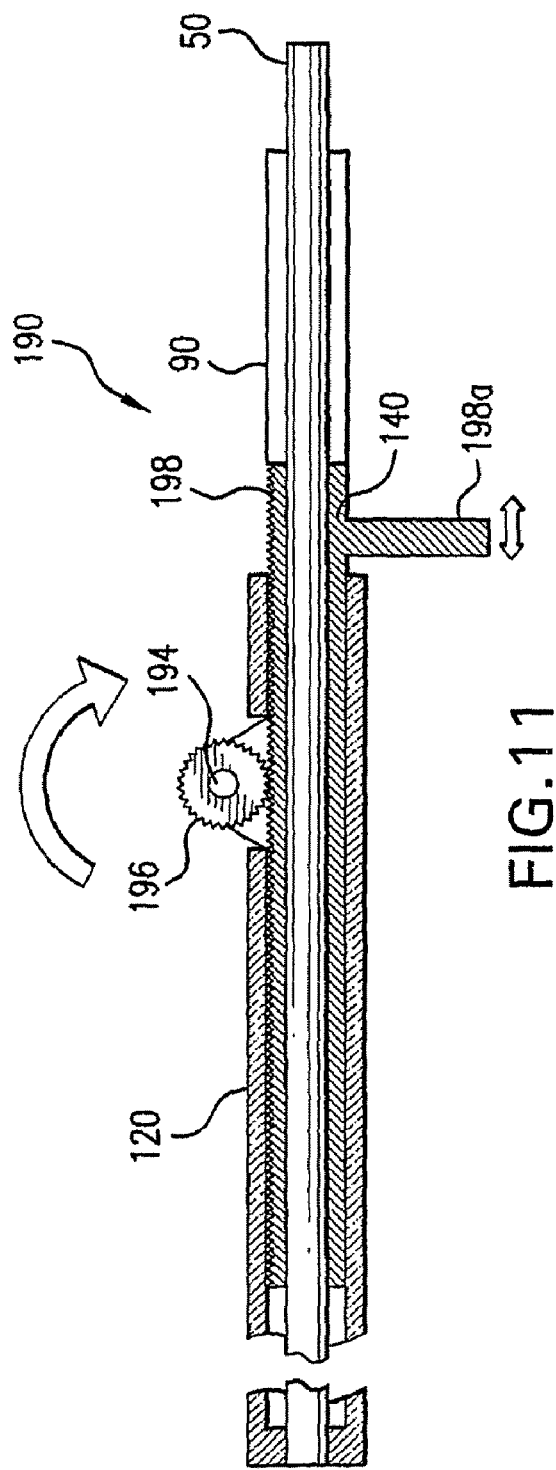
FIG. 11 is a partial cross sectional view of a proximal portion of an alternative delivery system in accordance with the invention.

In accordance with another aspect of the invention, a rack-and-pinion assembly as shown in FIG. 11 can be used. Rack-and-pinion assembly 190 includes a rotatable drive gear actuator 196, a first shaft 194 connected to the drive gear actuator 196. In accordance with this embodiment of the invention, shuttle 140 is attached to a rack 198. Rack 198 can be formed into the outer surface 256 of hypotube 250. Thus, rotational movement of actuator 196 is translated into longitudinal movement of shuttle 140 and sheath 90. Additionally, manual override 198a attached to rack 198 and/or sheath 90 can be provided, wherein the user can push on override 198 to move the sheath. Other methods and mechanisms are also within the scope of the invention. For example, retraction device such as a handle or spool could be connected to sheath by way of a pull wire (not shown).

Figure 12:
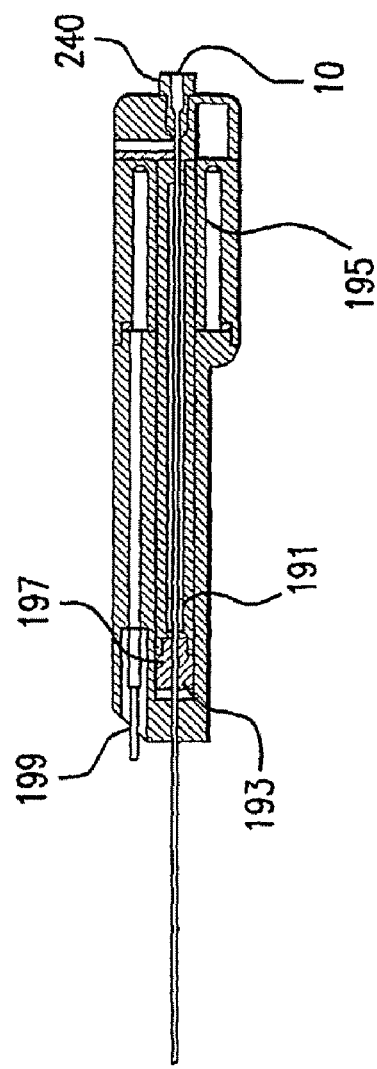
FIG. 12 is a cross sectional view of a proximal portion of an alternative embodiment of a delivery system in accordance with the present invention.

Similarly, sheath 90 could be retracted by using a system of hydraulically or pneumatically controlled pistons. In further accordance with the invention and as depicted in FIG. 12, a hydraulic system is depicted for retracting sheath 90. In accordance with this aspect of the invention, sheath 90 is affixed to a piston 191 having a seal 193 about its periphery. A supply of pressurized fluid 195, such as air or liquid saline solution, can be brought into fluid communication with a distal face 197 of piston 191 by opening valve 199. When valve 199 is in an open condition, the pressurized gas acts on distal face 197 of piston 191, causing it to be displaced in a proximal direction. Additionally, sheath 90 could also be retracted by using electromagnetic solenoids and/or drive motors.

In further accordance with another aspect of the invention, the delivery system includes a lock having an unlocked position permitting movement of the sheath, and a locked position prohibiting movement of the sheath.

Figure 13:
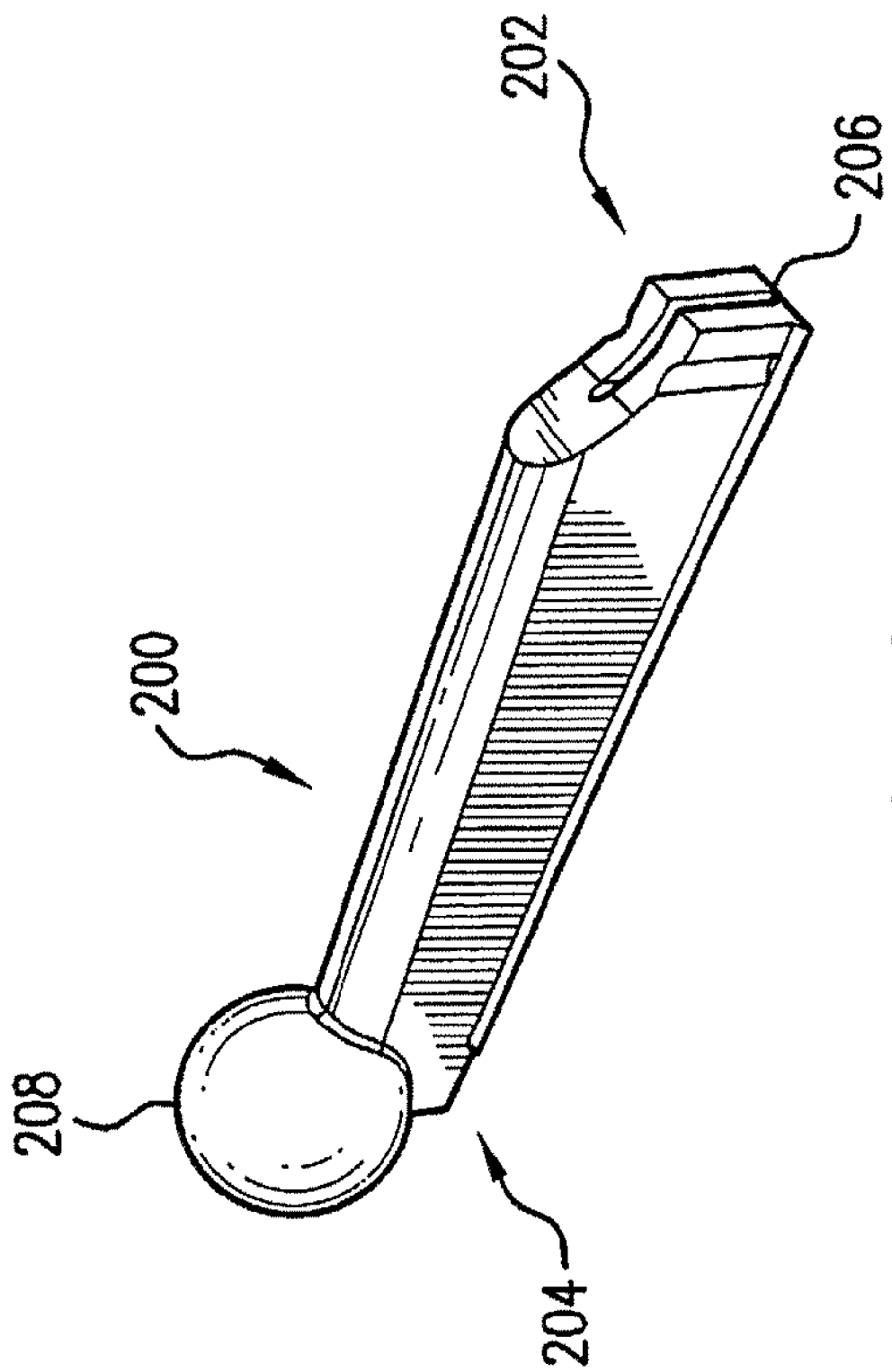
FIG. 13 is a perspective view of an actuator lock of the device of FIG. 1.
Figure 14B:
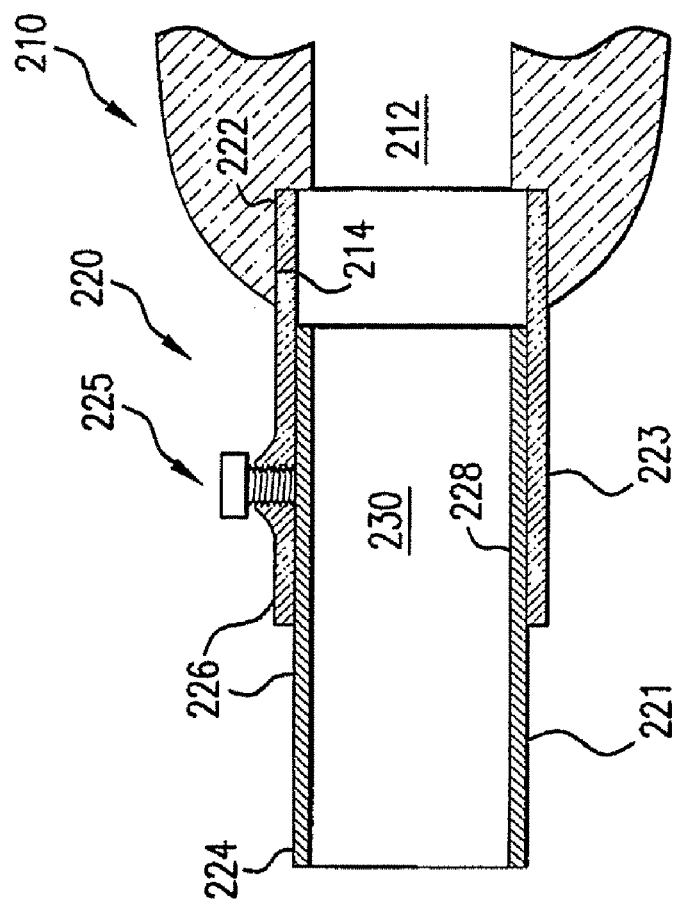
FIGS. 14(a)-14(c) are partial views of a stabilizer of the device of FIG. 1 and two alternative embodiments, respectively.
Figure 14A:
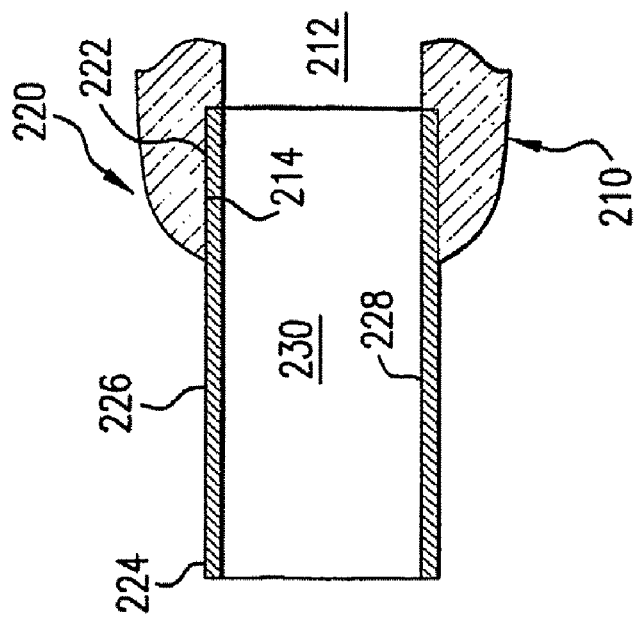
Figure 14C:
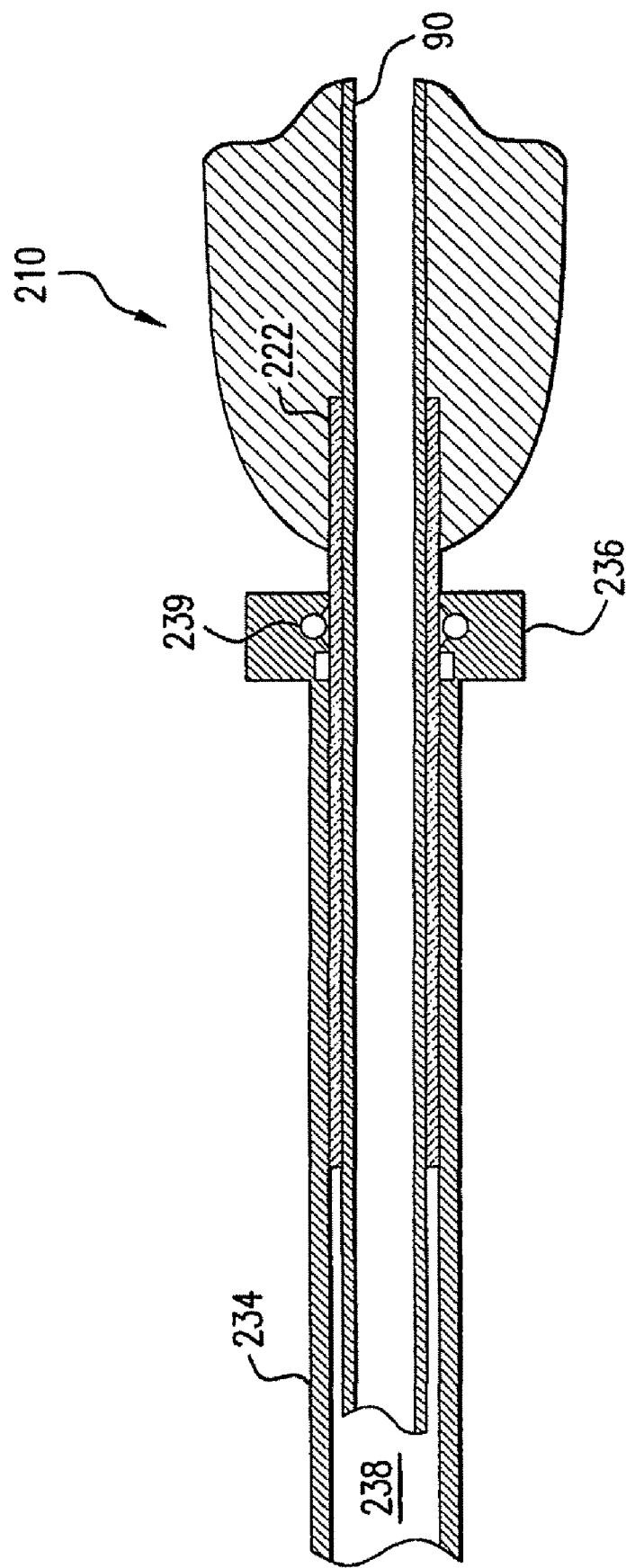

For purposes of illustration and not limitation, as embodied herein and as depicted in FIG. 13, a lock 200 is provided. The lock 200 prevents accidental deployment of the medical device 400 by preventing movement of the sheath 90 with respect to inner member 10. As depicted in FIGS. 1(a) and 13 lock 200 is provided in the form of an elongate member having a proximal end 202, a distal end 204, a longitudinal groove 206 and a knob 208 located at distal end 204. Lock 200 is installed and slidably disposed in a linear protrusion 182 in knob 180. Lock 200 has a locked position wherein the lock is engaged with a recess 214 in handle 120. In this position, lock 200 prevents rotational movement of knob 180 with respect to handle 120, and hence prevents longitudinal movement of sheath 90 (or the actuator) with respect to inner member 10. Lock 200 can be moved from its locked position in a distal direction with respect to handle 120 so that lock 200 disengages from recess 214 and is fully within the longitudinal length of knob 180. In this unlocked position, lock 200 no longer prevents rotational movement of knob 180 and thus sheath 90 can be moved by actuating actuator thereby permitting movement of sheath 90. A user presses on knob 208 to disengage or engage lock 200. In the unlocked position movement the sheath or the actuator is permitted.

As embodied herein, lock 200 is attached to knob 180. When moved from a locked position to an unlocked position, lock 200 also serves as a bearing surface for a user's thumb to facilitate rotational movement of knob 180 with respect to handle 120.

In another embodiment of the lock of the invention, the lock operates in a similar fashion as describe above but includes a locking lever 850 operationally engaged to the actuator and configured to releasably lock at least one of the actuator and sheath when in the locked position. The locking lever 850 is hingedly attached to the handle and also includes a detent 852, as depicted in FIGS. 21a-21d. The detent 852 engages the actuator and inhibits movement of the sheath. As embodied herein, the lock uses lever and/or cam action. As shown in FIG. 21a, the lever 850 is squeezed before the stent can be deployed. The lever 850 is configured to provide initial deployment of the stent once as it is actuated.

As depicted in FIGS. 21a-21d, the lock is operatively disposed to provide initial movement of the sheath when the lock is moved from the locked position to the unlocked position. The lock includes a cam to cooperate with the actuator to provide the initial movement.

In accordance with a preferred embodiment of the invention, lock 200 is formed of a polymeric or epoxy material containing approximately 20% fiberglass. However, other materials can be used. For example, a metallic material or other plastic or composite material may be used to form lock 200.

A variety of configurations can be used as a lock 200. For example, a sliding plate configuration need not be used for lock 200. A pushbutton locking device or rotatable member could be used. Similarly, a frangible member could be used whereby the frangible member is ruptured when a certain threshold torque is exceeded. Lock 200 could also include a key member (not shown) that would need to be inserted or removed in order to permit movement of the sheath 90.

In yet another alternative embodiment of the present invention, the handle comprises a gear assembly, wherein the gear assembly provides mechanical amplification of a user's input. The mechanical amplification can be utilized to remove the sheath 90 from covering the stent 400 in a non-linear manner. For example, it may be desirable to slowly remove the sheath initially and then remove the sheath quickly after a portion of the stent has been delivered. Additionally, endoprosthesis, become longer the force necessary to retract the sheath increases, thereby requiring more user applied force to deploy the stent which may lead to misplacement or damage to the endoprosthesis. Therefore, it is desirable to provide a delivery system capable of quickly delivering these longer length endoprosthesis'.

In accordance with another aspect of the invention, as depicted and embodied in FIGS. 17a through 20h, a delivery system includes an actuator on the handle and coupled to a rack-and-pinion assembly. The rack-and-pinion assembly is moves the sheath with respect to the inner member along the longitudinal axis from the first sheath position to the second sheath position. Further, the rack-and-pinion assembly is configured to increase the deployment rate of movement for the sheath during at least a portion of movement of the actuator.

Figure 17A:
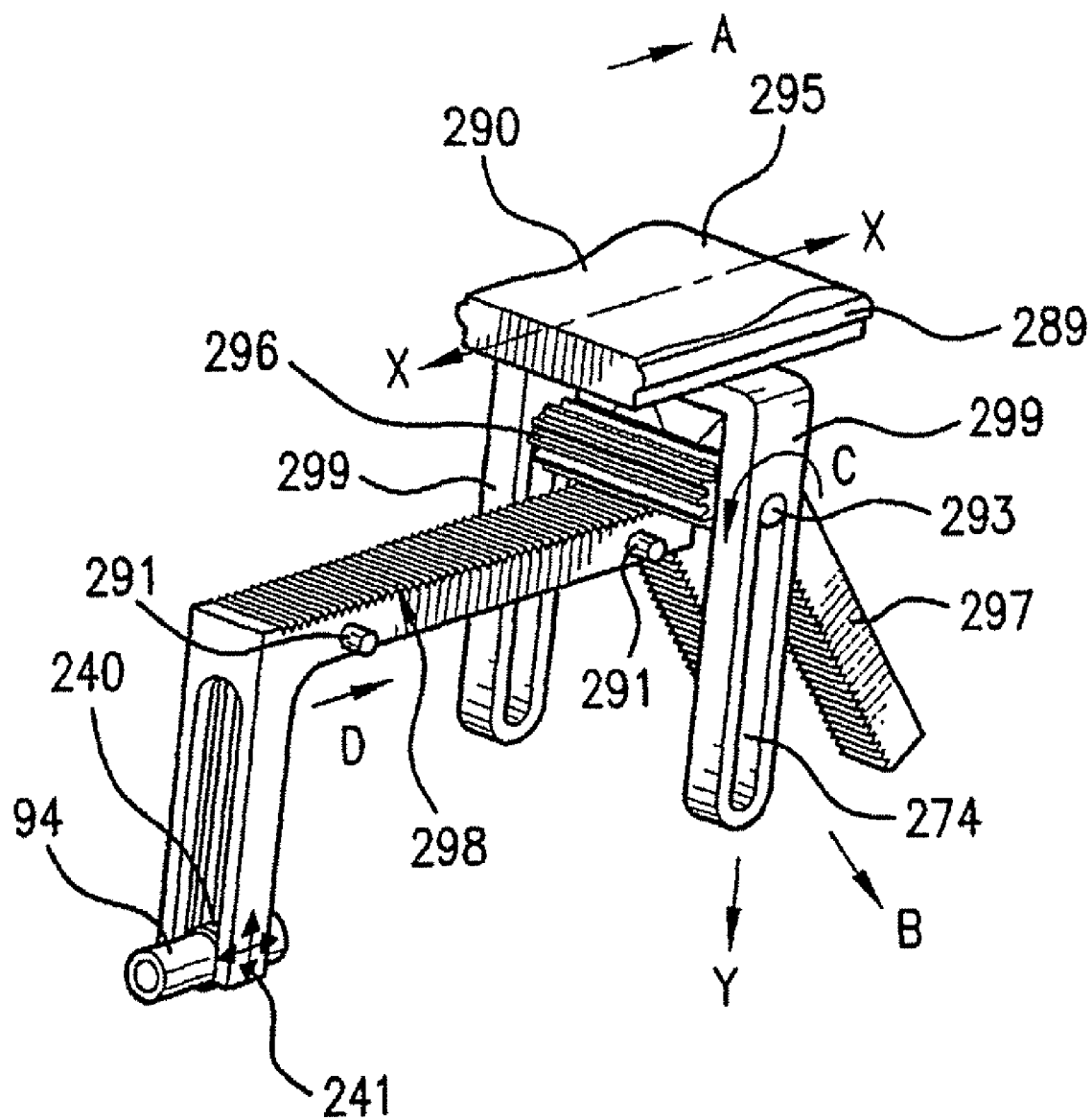
FIG. 17a through 17c are partial views of an alternative embodiment of a sheath retraction mechanism in accordance with the present invention.
Figure 17B:
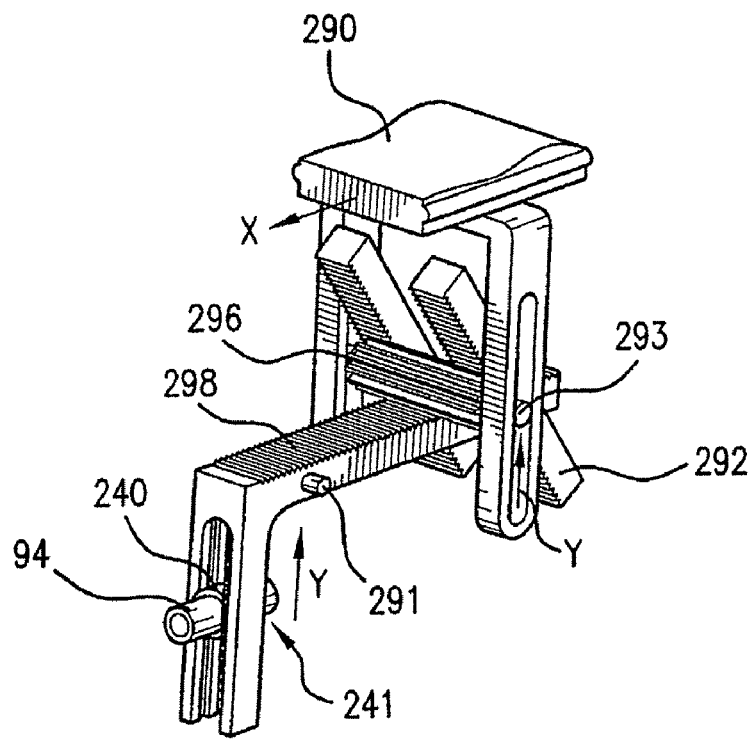
Figure 17C:
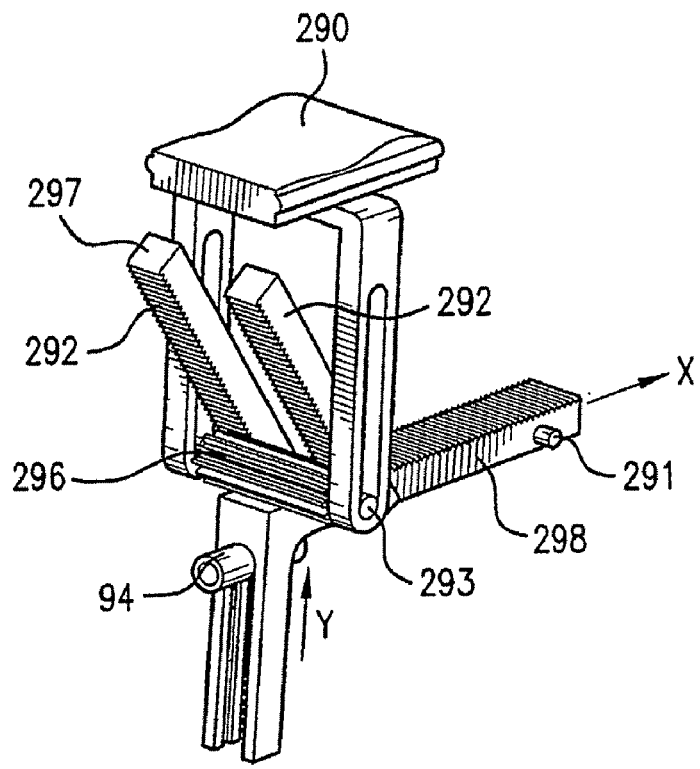

As depicted in FIGS. 17a through 17c, the rack-and-pinion assembly includes a first gear rack 298, a second gear rack 297 and a pinion gear 296. The second rack 297 is disposed adjacent the first end of the first rack 298 and at an angle relative thereto. For example and not limitation, the first rack 298 is disposed at an angle less than ninety degrees relative to the second rack 297. The first gear rack 298 is moveable relative the second gear rack 297 and the pinion gear 296 is operatively coupled to the first and second gear racks, respectively. In further accordance with one embodiment of the invention, the first gear rack 298 is coupled with the sheath 90 at its proximal end 94.

As depicted in FIG. 17a through 17c, each of the first rack 298 and the second rack 297 include a plurality of gear teeth along a length thereof, respectively. In one embodiment, the first rack 298 has a different number of teeth than the second rack 297.

As depicted herein, the first rack includes pins 291 configured to be received within a track provided on the handle 120. The pins 291 are disposed adjacent to and perpendicular to the plurality of gear teeth. The pins 291 are configured to be received within grooves (not shown) formed in the handle 120 as previously shown, wherein the grooves define a path which the first rack 298 would travel along in use.

In a further aspect of the invention, the actuator can include a slider 295, which is operatively coupled to the pinion gear 296. The slider 295 is moveable in a linear direction. In accordance with one embodiment, slider 295 includes first and second extenders 299 extending therefrom. Each extender includes a slot 294 defined therein. As shown in FIG. 17a, each end 293 of the pinion gear 296 slidingly engages a respective one of the slots 294 defined in each of the first and second extenders 299. Each of the first and second ends of pinion gear 296 can further include shaft 293 slidably disposed within the slot 294 and through an axis of the pinion gear 296. The shaft 293 is configured to slide within the slot 294 and allow the pinion gear 296 to rotate.

As depicted in FIGS. 17A-C the first rack 298 is operatively coupled to the pinion gear 296 and the plurality of gear teeth of the second rack 297 operatively engage with the pinion gear 296. In this manner, movement of the slider 295 engages the pinion gear 296 along the second gear 297 rack to rotate the pinion gear 296, which in turn engages the first gear rack 298 for linear movement thereof. In this regard, the engagement of the pinion gear 296 with the second rack 297 due to the movement of the slider 295 results in movement of the first rack 298 in the linear direction at a rate greater than the movement of the slider 295. The second rack 297 is fixedly attached to the housing 120 (not shown) and does not move during use. In accordance with an alternative embodiment of the invention, the plurality of gear teeth disposed on each rack have a different pitch, thereby providing a force amplification system.

Preferably, as embodied herein, the second rack 297 includes a pair of elongate members 292, as shown in FIG. 17c. Each elongate member 292 includes a plurality of teeth in engagement with the pinion gear 296.

In yet another aspect of the invention, as embodied herein and depicted in FIG. 17a-18c, a shuttle 240 is slidably disposed at the second end of the first rack. The shuttle 240 is connected to the proximal end 94 of the sheath 90 as described herein.

As shown in FIG. 17*a*, the two rack assembly is shown in an initial position, wherein the distal end of the sheath 90 would be covering the seat 116 and the stent 400. To deploy the stent 400 from the seat 116, a user would apply a force to the slider 295, wherein the slider 295 would translate along an axis as indicated in FIG. 17 by line X-X. As the slider 295 translates along a length of the handle 120 while the pinion gear 296 rotates. As the pinion gear 296 rotates, the first rack 298 is translated and the pinion moves down the second rack 297 as shown in FIG. 17*b*. Additionally, as the first rack is translated, the shuttle 240 attached to the proximal end of the sheath 94 slides within the groove 241 formed in the first rack 298.

Referring now to FIG. 17*c* there is shown the rack-and-pinion assembly wherein the slider 295 has been translated to a final position and the sheath 90 has been removed from covering the seat 116 and the stent 400 (not shown). As shown in FIG. 17*c*, the first rack 298 and the pinion 296 are disposed at the bottom of the second rack 297. In this regard, in operation, as shown in FIG. 17*a*, the slider 290 is moved in direction A by a user. This results in the pinion gear 296 moving down the second rack 297 in direction B, which in turn results in rotation of the pinion gear 296 in direction C. This draws the first rack 291 direction D which results in the retraction of the sheath 94.

Preferably, and as embodied herein, the ratio of movement of the sheath to movement of the actuator can be greater than 1:1 during at least a portion of movement of the actuator. For the purpose of illustration and not limitation, the rack-and-pinion assembly shown in FIGS. 17*a*-17*c* provides the user with a two to one ratio, that is for every 1 cm the slider 295 is moved, the distal end of the sheath moves 2 cm. This increased sheath retraction is desirable for retracting sheaths covering long stents.

In further accordance with the invention, the ratio of movement of the sheath to movement of the actuator can vary. Alternatively, however, the ratio of movement of the sheath to movement of the actuator can be constant, if desired.

Figure 18A:
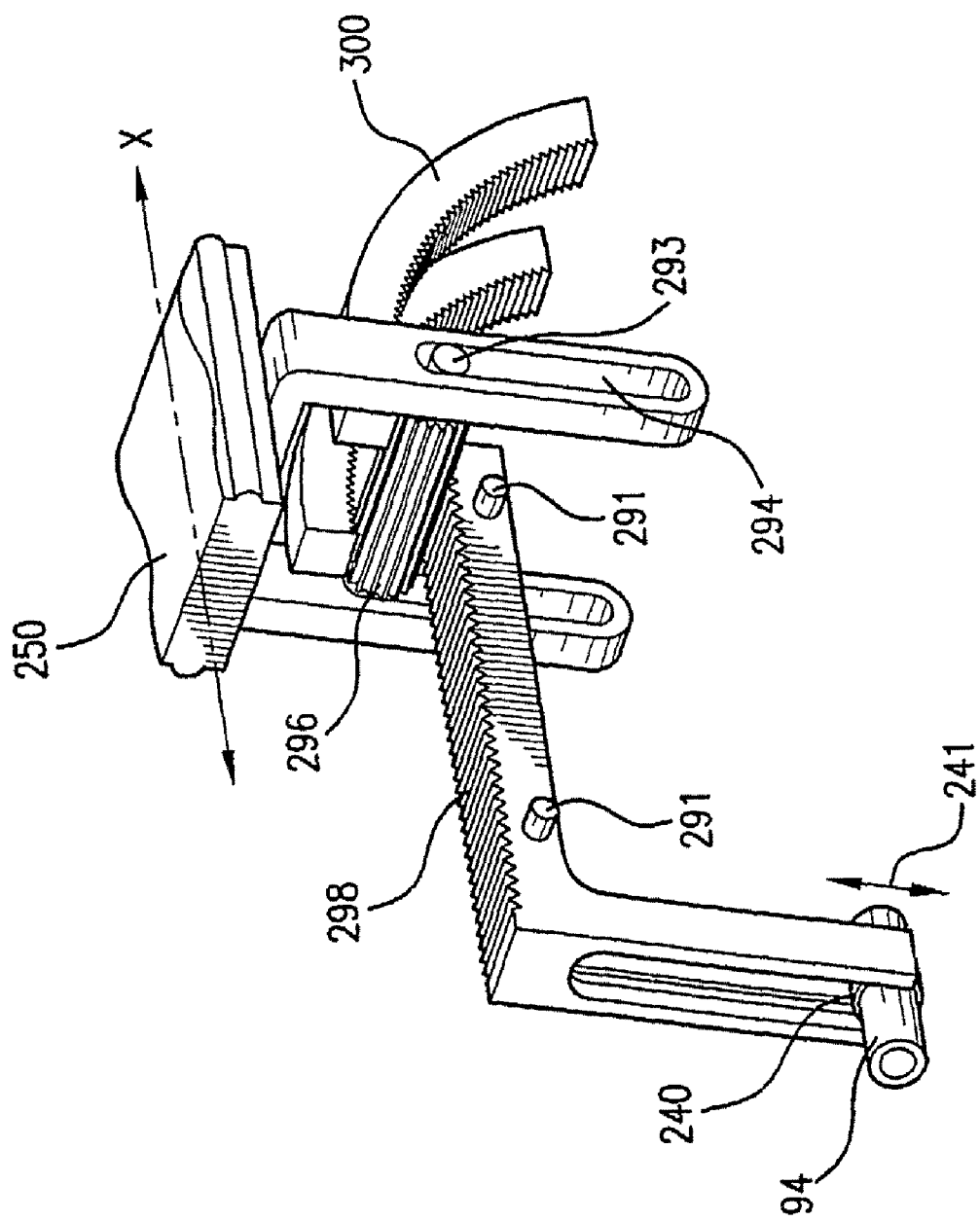
FIGS. 18a through 18c are partial views of an alternative embodiment of a sheath retraction mechanism in accordance with the present invention wherein the sheath is retracted in a non-linear manner.
Figure 18B:
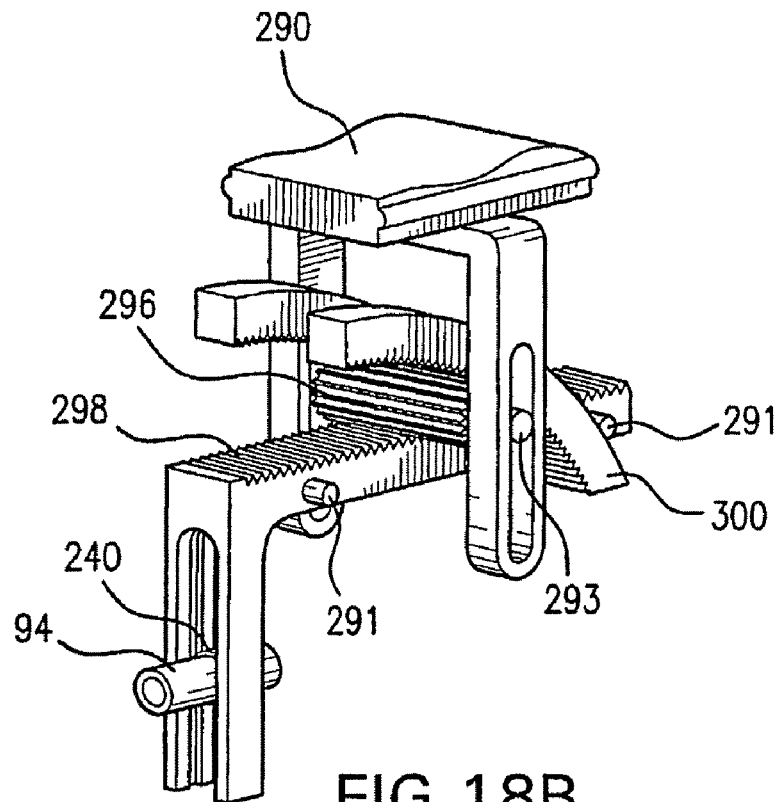
Figure 18C:
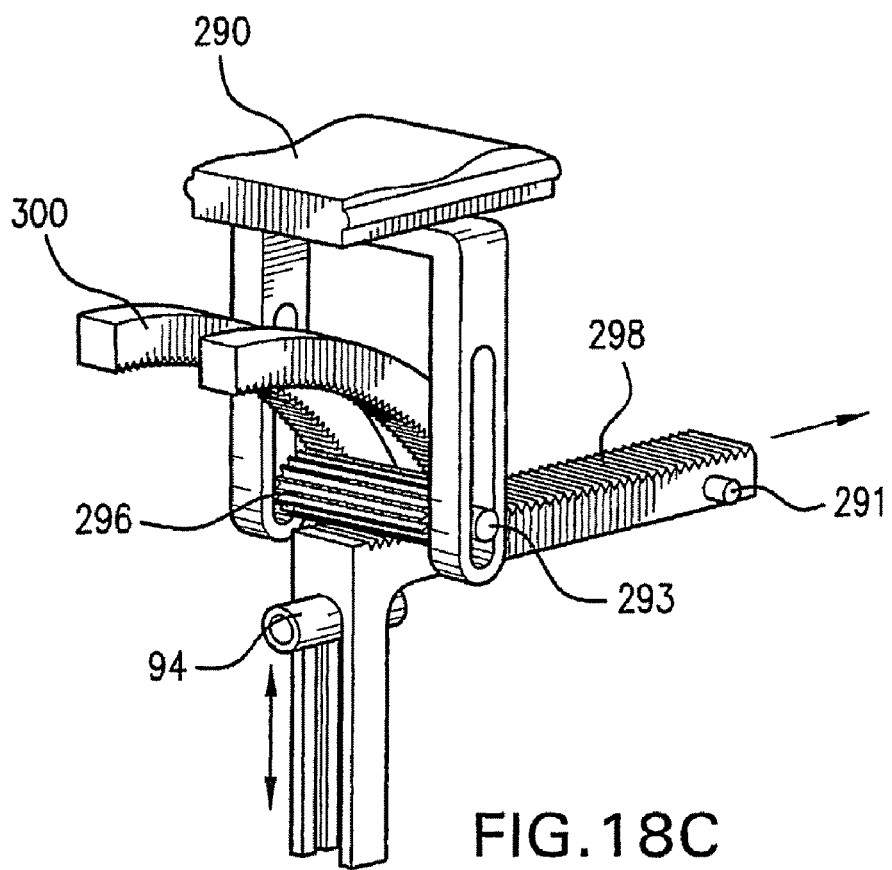

In another embodiment of the invention, as shown and depicted in FIGS. 18*a* through 18*c*, the rack-and-pinion assembly includes a second rack 300 configured as a non-linear member. For example and not limitation, the non-linear member can be arc-shaped. In this manner, the second rack 300 as embodied in FIGS. 18*a*-18*c* provides non-linear sheath movement.

As embodied herein, as a force is initially applied to the slider 295, the slider slides back in a channel formed in the handle 120 (not shown), wherein the pinion gear 296 rotates, causing the first rack 298 to translate. As the pinion gear 296 rotates and the first rack 298 translates, the pinion gear 296 advances along the arc of the second rack 300. Initially, the pinion gear 296 and the first rack 298 slowly advance along the arc of the second pinion gear 300. As the pinion gear 296 and first rack 298 continue to advance along the arc of the second rack 300 the rotational speed of the pinion gear increases, thereby increasing the translation speed of the first rack. Thus, the rack-and-pinion handle assembly illustrated in FIGS. 18*a*-18*c* causes non-linear sheath movement. Initially, the sheath will be slowly retraced from covering the stent, wherein as the slider is advanced at a constant rate, the sheath will be removed more rapidly without requiring change of input from the user.

In accordance with other embodiments of the invention, as embodied herein and depicted in FIGS. 19*a* through 20*i*, the delivery system includes a two-rack assembly for the delivery of a medical device. A slider 402 is located on a handle 404 and is configured to move a sheath 406 along a longitudinal axis from a first sheath position to a second sheath position (not shown) thereby delivering a medical device. The assembly includes two substantially round gears 401 sandwiching a pinion 408 and the slider 402. The slider 402 is located on top of but detached from the pinion 408. In The slider 402 and pinion 408 are each configured to interact with the gears 401 so that the sheath 406 is retracted a distance greater than the distance that the slider 402 is moved.

As embodied herein and as depicted in FIGS. 19*a*-20*i*, the rack-and-pinion assembly includes a pinion 408 having a plurality of teeth along its length and a rack gear 401 having a circumferential surface and being rotatable about a center axis. The pinion gear has a first gear pitch 410 operatively coupled with the pinion 408 and a second gear pitch 412 vertically displaced on a height of the circumferential surface.

Preferably, the actuator 402 includes a slider 405 having an elongate surface 403 with a plurality of teeth therealong. The plurality of teeth of the slider 405 are operatively coupled to a second gear pitch 412 of the rack gear 401 for rotation of the rack gear 401 upon linear movement of the slider 405. In this manner, the different gear pitches allows the pinion 408 to be displaced a distance greater than the slider 405. The ratio of displacement depends on the ratio of the first and second gear pitches.

Figure 19A:
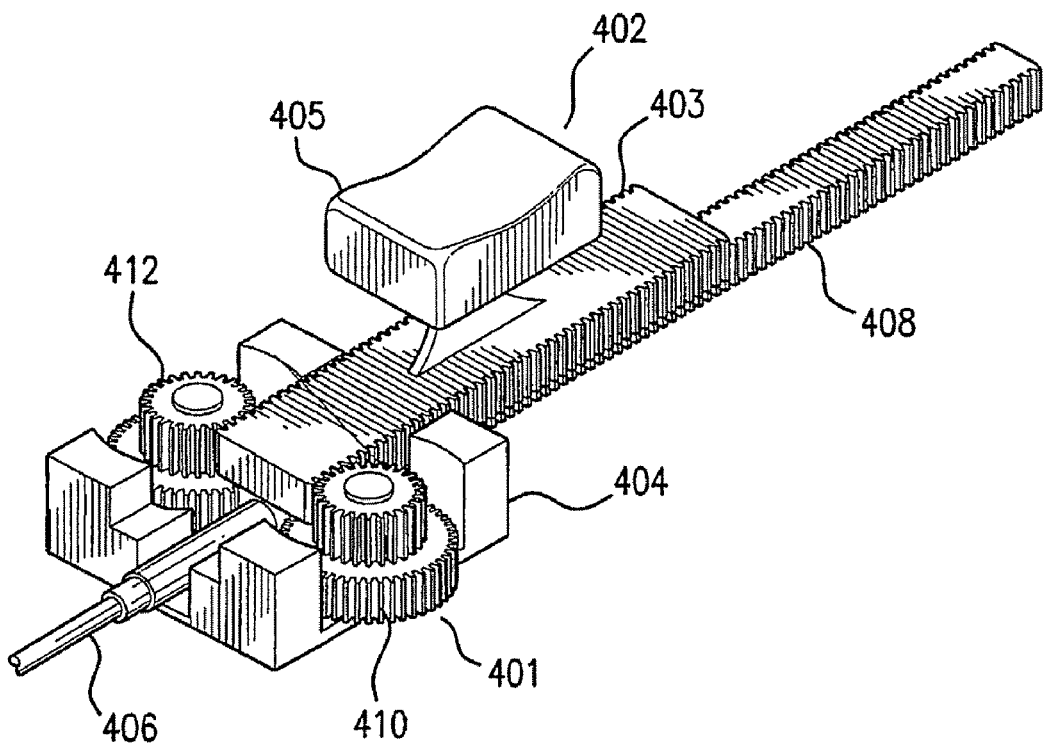
FIGS. 19a through 19b are partial views of an alternative embodiment of a sheath retraction mechanism in accordance with the present invention.
Figure 19B:
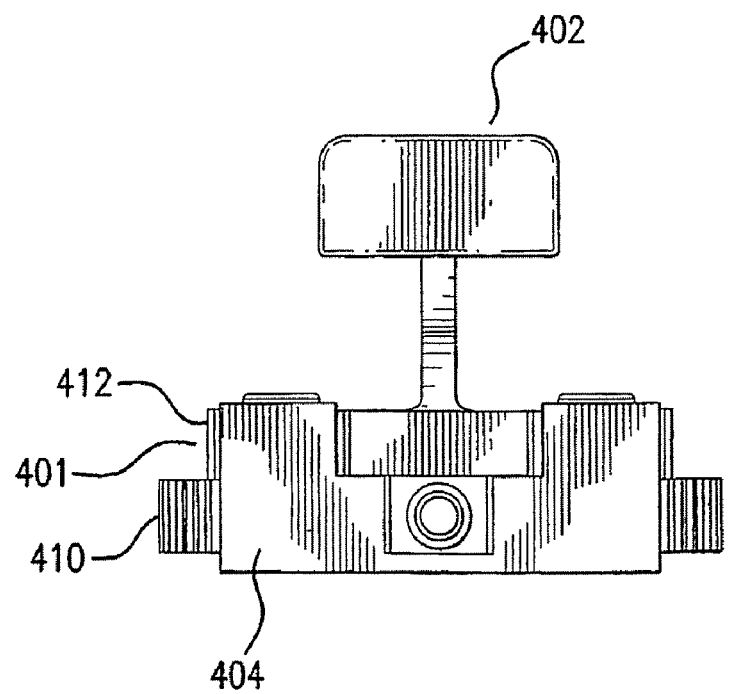

In one embodiment, as shown in FIGS. 19*a*-19*b*, the first gear pitch is defined by a first generally cylindrical portion 410 of the rack gear 401. The rack gear 401 has a first diameter and the second gear pitch is defined by a second generally cylindrical portion 412 of the pinion gear having a second diameter. The first diameter is greater than the second diameter. Rotation of the rack gear 401 due to linear movement of the slider 405 results in a greater rate of movement of the pinion 408. The pinion 408 is operatively coupled to the sheath 406.

In an alternative embodiment, as depicted in FIGS. 20*a*-20*i*, the rack gear 401 is a bevel gear that has a generally conical circumferential surface 412. The second gear pitch is varied along a height of the conical surface 412. The plurality of teeth of the slider 402 are disposed at varied heights along the elongate surface 403. Linear movement of the slider 402 results in varied engagement of the plurality of teeth along the height of the circumferential surface 412 to vary the rate a rotation of the rack gear 401 and the rate of movement of the pinion 408.

Figure 20F:
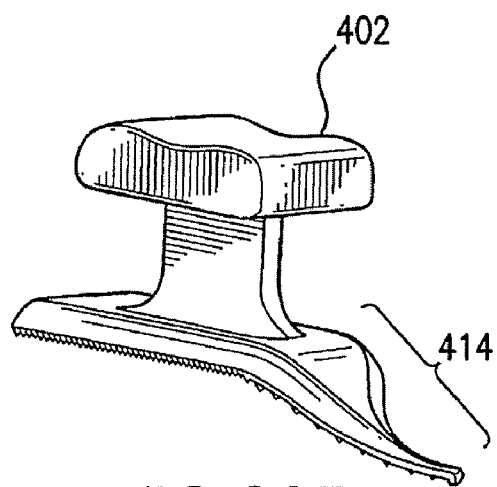
Figure 20G:
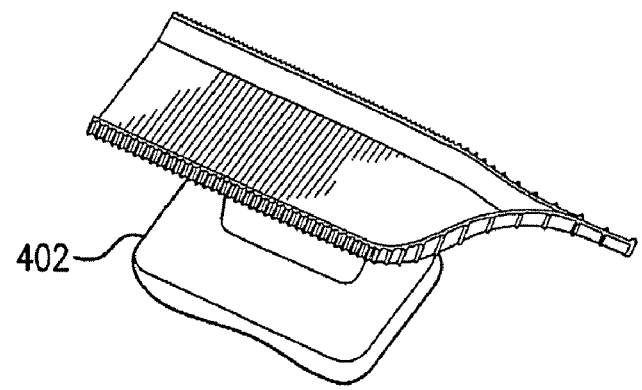
Figure 20H:
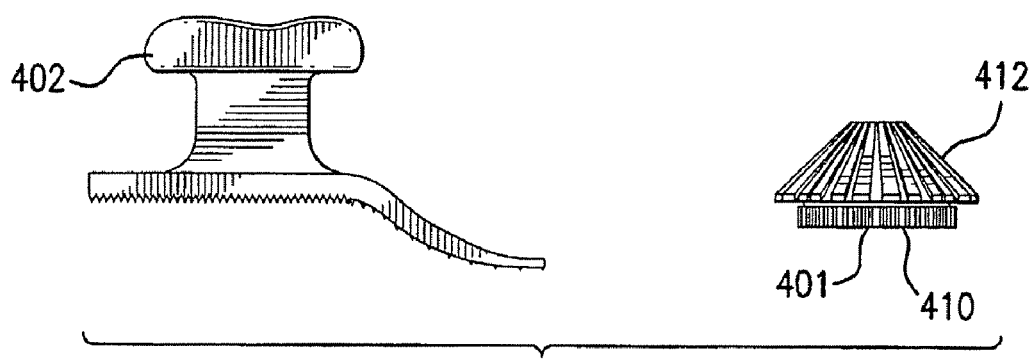

As shown in FIGS. 20*f*, 20*g*, and 20*h*, the plurality of teeth of the slider vary in pitch along a length of the elongate surface 403.

As shown in FIGS. 19*a* and 20*a*, the rack-and-pinion assembly includes a second rack gear 401 and the pinion 408 is disposed between the first and second rack gear 401.

Referring now to FIGS. 19*a* and 19*b*, this assembly can be configured using gears that have two sections. Each of the two racks gears 401 has a lower section 410 and an upper section 412 such that the upper section 412 has a diameter smaller than the lower section 410. The thumb slide 402 engages with the upper section 412 and the pinion 408 engages with the lower section 410. The ratio of movement of the sheath 406 to the thumb slide 402 is greater than 1:1. The ratio can be 2:1, for example, if the upper section 412 has a diameter that is half of the diameter of the lower section 410.

The rack-and-pinion assembly of FIGS. 20*a*-20*i* is similar to that shown in FIGS. 19*a*-*b*, wherein the same or similar reference numbers have been utilized to describe the same or similar components.

Figure 20I:
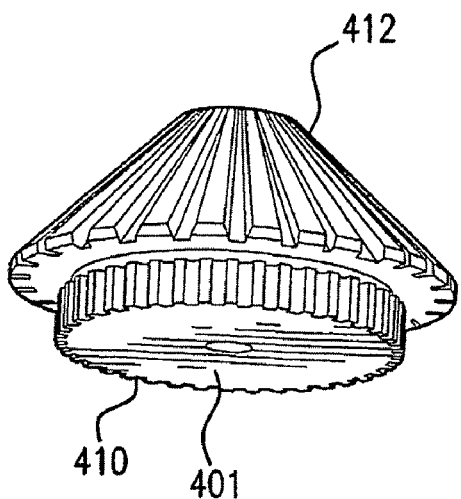

In this embodiment, the round rack gears 401 are configured as bevel gears 401 as shown in FIG. 20*i*. The bevel gears 401 have an upper portion 412 with variable gear spacing and a lower portion 410 with a constant gear ratio.

The lower portion 410 is configured to retract the sheath 406 and the upper portion 412 is configured to interact with the thumb slide 402. The thumb slide 402 also includes a nose portion 414 with variable gear spacing to correspond with the variable gear spacing of the bevel gears 401. The variable gear spacing is configured to provide the following ratios of sheath thumb slide 402 movement to sheath 406 retraction distance: less than one to one during positioning of the medical device, for example 1:1.25 as shown in FIG. 20*c*; approximately one to one during a transition period as shown in FIG. 20*d*; and greater than one to one during and after deployment of the medical device, for example 2.5 to 1 as shown in FIG. 20*e*.

In accordance with another aspect of the invention, a delivery system in accordance with the invention can be provided further including a stabilizer disposed about the inner member and extending from the handle.

For purposes of illustration and not limitation, as embodied herein and as depicted in FIGS. 1(*a*) and 14(*a*), a stabilizer 220 is provided having a proximal end 222, a distal end 224, an exterior surface 226, and an interior surface 228 with a lumen 230 defined therethrough. Stabilizer 220 is preferably a tubular member disposed about sheath 90 and attached at its proximal end 222 to nose 210. Specifically, proximal end 222 of stabilizer can be fitted into an enlarged diameter portion 214 of lumen 212 in nose 210. The two parts may be joined by adhesive bond, may be melted together, or connected in other various ways as are known in the art including threaded connections, press fit connections and the like.

Stabilizer 220 is preferably a flexible member capable of at least one degree of movement. For example, stabilizer 220 can be provided in the form of a coil spring or other flexible tubular member capable of bending along its longitudinal axis upon the application of a transverse force. Lumen 230 of stabilizer 220 is configured to permit sheath 90 to pass freely therethrough. With reference to FIG. 14(*c*), the external surface 226 of stabilizer 200 can be configured to fit into a guide sheath 234 with an introducer valve 236 that has already been introduced into a patient's lumen. The guide sheath 234 defines a lumen 238 that permits passage of delivery system 300. Introducer valve 236 provides for a liquid tight seal. Optionally, an o-ring 239 or other seal can be provided. Introducer valve 236 can also be provided in the form of a pierced membrane that surrounds sheath 90 or stabilizer 220. The liquid tight fit between stabilizer 220 and guide sheath 234 thus does not impede retraction of sheath 90 when actuator 130 is actuated. Thus, it is possible to introduce delivery system 300 into a patient, deliver a medical device 400 and withdraw delivery system 300 with minimal blood loss to the patient. The stabilizer 220 may be constructed having a length proportional to the overall length of the delivery system 300. In a preferred embodiment, the ratio between the stabilizer and the overall length of the delivery system 300 is about 2:1.

In an alternative embodiment depicted in FIG. 14(*b*), stabilizer 220 can have an adjustable length. In accordance with this aspect of the invention, stabilizer has a distal reduced diameter portion 221 that is slidably received in a proximal, increased diameter portion 223. A fixation member 225 can also be provided to fix the position of the two portions 221, 223 of stabilizer 220 with respect to each other. Optionally, distal portion 221 can be threadably received in proximal portion 223. In accordance with this aspect of the invention, portions 221, 223 can be provided in the form of concentric coil springs where the pitches are chosen such that one is threadably received inside of the other. It is further contemplated that the distal reduced diameter portion 221 may be utilized independently of the increased diameter portion 223.

Stabilizer 220 may be made from a metallic material such as stainless steel, but other materials can be used. For example, stabilizer can be of a braided shaft design, a multi-layer design, or other polymeric extrusion.

Additionally or alternatively, a strain relief (not shown) disposed about the stabilizer 220 can be provided. The strain relief is configured to reduce the stress concentration at the juncture between the stabilizer 220 and the nose 210. Such a strain relief is made, for example, from HS 101 irradiated polyolefin that can be obtained from Insultab, Inc., although any suitable material of construction can be used.

In accordance with an additional aspect of the invention, the delivery system can be configured such that the sheath and inner member define an annular space therebetween, wherein the annular space is arranged in fluid communication with a flush port to permit a fluid to pass therethrough.

For purposes of illustration and not limitation, as embodied herein and as depicted in FIG. 2, flush port 240 is arranged to be in fluid communication with the annular space 242 defined between the outer surface 60 of bumper 50 and the inner surface 102 of sheath 90. Shuttle 140 is sized and shaped to be received by recess 134 in nosepiece 132. O-rings 158 are configured to provide a liquid-tight seal between shuttle 140 and wall portion 136 of recess 134 when a liquid is flushed through flush port 240. In addition, a shuttle flush lumen 149 (See FIGS. 1(*d*) and 2) is provided to permit fluid to pass through outer space 243 shuttle to access annular space 242. When a fluid agent, such as saline, is flushed through flush port 240 and annular space 244, o-rings 158 prevent the saline fluid from moving past shuttle 140 into handle 120. A hose 246 can also be attached to flush port 240, preferably by way of adhesive connection, although other joining techniques are appropriate.

In accordance with another embodiment of the invention, a flush port 240 can also be fitted onto proximal end 12 of inner member 12 (See FIG. 12). Such a flush port can be used for flushing lumen 18. Such a flush port can further include an adaptor (not shown) in fluid communication with the lumen.

Flush port 240 can take on a variety of forms. In accordance with an alternative embodiment of the invention, Flush port 240 can be provided with a non-return valve. In accordance with this aspect of the invention, a non-return valve (not shown) can be attached to flush port 240 to permit a positively pressurized stream of flushing fluid (e.g., saline solution) to pass through flush port 240, but prevent air from passing into flush port 240 after the stream of flushing fluid is disconnected. The non-return valve can be, for example, a check valve that includes an elastic member biased to keep the valve in a closed condition. The elastic member can be provided in the form of a spring. Alternatively, a membrane of elastic material containing an orifice could be used, whereby a positively pressurized fluid can pass through the orifice but air at atmospheric pressure cannot. Such a non-return valve is preferably used to direct a beneficial agent though channel 53 of device 300 to a predetermined location in a patient.

Figure 16:
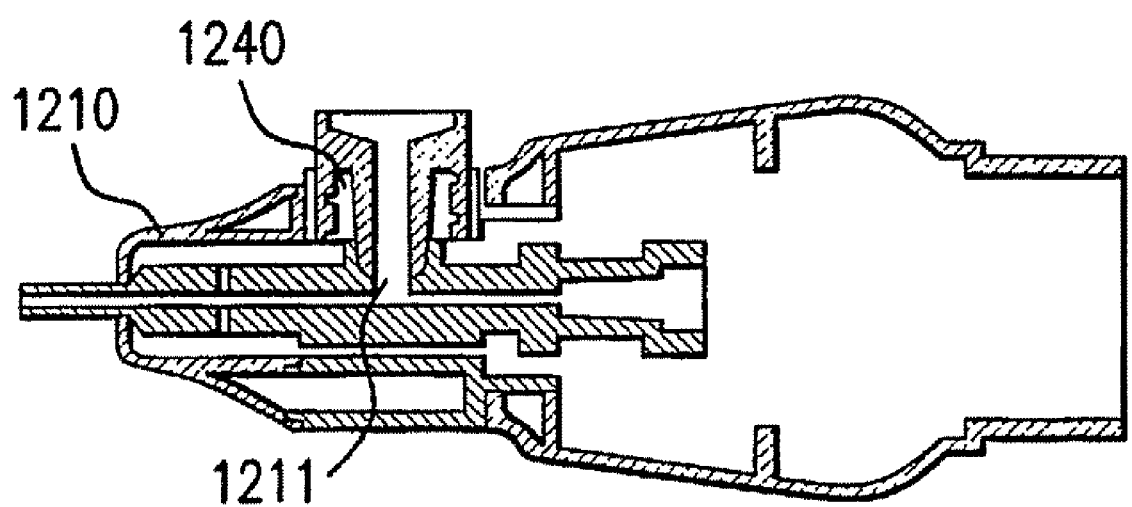
FIG. 16 is a cross sectional view of an alternative nose design of the delivery device in accordance with the present invention.

An alternative embodiment of the nose 210 can be seen in FIG. 16, wherein the nose 1210 as illustrated in FIG. 16 includes a flush port 1240. Nose 1210 further includes a valve 1211 wherein the valve 1211 eliminates the o-rings 158 of the shuttle assembly, thereby reducing friction within the system. As shown in FIG. 16, the flush port 1240 is configured to directly receive the distal end of a syringe, for example, the flush port 1240 may be constructed having geometry similar to that of a luer fitting, thereby allowing the delivery system to be flushed with the use of a conventional syringe.

In further accordance with the invention, the delivery system can further include a hypotube 250 disposed about the inner member 10.

For purposes of illustration and not limitation, as embodied herein and as depicted in FIGS. 1(d) and 2, hypotube 250 has a proximal end 252, a distal end 254, an outer surface 256, and a lumen 148 defined therethrough. As embodied herein, hypotube 250 is disposed about inner member 10. Distal end 254 of hypotube 250 is proximal to the proximal end 52 of the bumper 50. Proximal end 252 of hypotube 250 is adjacent to distal end 276 of adjustment hypotube 272, discussed in detail below. Hypotube 250 may be made of a metallic material, but may also be made from a polymeric material or may be a resin-impregnated fiber reinforced member.

Hypotube 250 is preferably connected near its proximal end 252 to a connector 260. Connection may be achieved, for example, by way of adhesive bond, threaded or keyed connection, force fit, or the like. Connector 260, in turn, is in abutting relationship with proximal end 172 of thumbscrew 170, such that thumbscrew 170 can rotate with respect to connector 260.

Connector 260 is preferably made from a plastic material such as ABS plastic, but may also be made from other polymeric or metallic materials.

In accordance with a representative embodiment of the invention, hypotube 250 has a length of about 1.6 inches, an external diameter of about 0.065 inches and an inside diameter of about 0.05 inches. Hypotube 250 may be made from stainless steel, although other materials can be used. For example, plastic materials and/or composite materials such as single or multilayer extrusions can be used. It will be understood that dimensions can vary depending on the intended use of delivery system 300.

In further accordance with the invention, a medial portion 121 of handle 120 including gripping surface 126 can be attached onto connector 260, preferably by way of adhesive bond. As depicted in FIG. 2, an external threading 262 is provided on connector 260 to provide an attachment point for complementary threading 123 on medial portion 121 of handle 120, although other joining techniques can be used, such as adhesive bonding, solvent welding and the like.

The delivery system in accordance with the invention also can include an adjustment member configured to move the inner member with respect to the sheath.

For purposes of illustration and not limitation, as embodied herein and as depicted in FIG. 2, adjustment member 270 includes an adjustment hypotube 272 disposed about the proximal end 12 of inner member 10. Adjustment hypotube 272 is preferably attached to inner member 10 and has a proximal end 274 and a distal end 276. Adjustment member 270 can further include a hub 278 fixedly attached to the proximal end 274 of the adjustment hypotube 272. Distal end 276 of adjustment hypotube 272 is disposed adjacent hypotube 250. Adjustment hypotube may be made of metal, but also may be made from a polymeric of fiber-reinforced resin material.

In further accordance with the invention, the adjustment member can include an adjustment lock where the adjustment lock has a locked position to prevent the inner member from being displaced longitudinally with respect to the sheath and an unlocked position to allow the inner member to be displaced longitudinally with respect to the sheath.

For purposes of illustration and not limitation, as embodied herein and as depicted in FIG. 2, adjustment lock 280 is provided. Adjustment lock 280 can be provided at proximal end 122 of handle 120. As embodied herein, adjustment lock is provided in the form of a body having a collet 282 (not shown) that is threaded into threads 125 located at distal end 124 of handle 120. In operation, when adjustment lock 280 is in a locked position, collet 282 clamps down on adjustment hypotube 272, and adjustment member 260 and inner member 10 cannot move longitudinally with respect to sheath 90 without actuating actuator 130. However, when adjustment lock 280 is in an unlocked position, relative movement between inner member 10 and sheath 90 can be achieved without actuating actuator 130. In this manner, small adjustments can be made by a physician to align sheath 90 with tip 30 before use of delivery system 300. Such adjustments can be necessary if inner lumen 10 elongates in the process of sterilization.

For purposes of illustration and not limitation, as depicted in FIG. 15, in further accordance with the invention, when delivery system 300 is provided with more than one seat 116 to permit delivery of more than one medical device 400, adjustment member 270 (see FIG. 2) can be used to realign the distal end 98 of sheath 90 with tip 30 after a medical device has been delivered. For example, after a first medical device, such as a stent 400a, is delivered, seat 116a is exposed, and sheath 90 is still covering medical device 400b. By unlocking adjustment lock 280, inner member 10 and tip 30 can move longitudinally with respect to sheath 90, bumper 50b-n, and medical device 400b. Inner member 10 is then moved in a proximal direction with respect to sheath 90. In the process, bumper 50a, which is preferably freely disposed over inner member 10, is urged against medical device 400b, and the distal end 98 of sheath 90 is brought into contact with tip 30, and the adjustment lock 280 is locked to prevent bumpers 50a-50n and medical devices 400b-400n from moving with respect to sheath 90 or inner member 10. Delivery system 300 can then be displaced to a different location within the patient to deliver subsequent medical devices 400b-400n. The ability to deliver multiple medical devices without removing delivery system 300 from the patient can decrease the total amount of time necessary for the medical procedure. This arises from eliminating the need for preparing and introducing multiple delivery systems to the patient. In addition, introducing a single delivery system into a patient instead of multiple devices also reduces trauma to the patient.

Moreover, in the embodiment of the invention in FIG. 15, it would also be possible to equip each bumper 50a-50n with channels 53a-53n (not shown) as described in detail above to direct a beneficial agent to a predetermined location in a patient. Thus, each time a medical device 400a-400n is delivered, it is possible to direct a beneficial agent through channels 53a-53n and/or via material deposited in perforations 64 in each bumper segment 50a-50n. An agent to release beneficial agent in perforations 64 can additionally or alternatively be introduced through flush port 240 and directed through channels 53a-53n to a predetermined location in a patient.

In further accordance with the invention, the delivery system also includes a method of assembling a delivery system for delivering a medical device. The method includes providing a sheath, providing a bumper, positioning the bumper into the sheath, providing a medical device, disposing the medical device in the sheath, providing an inner member having a tip formed at a distal end thereof, placing the inner member through the medical device and the bumper, and positioning a handle over the inner member. For purposes of illustration and not limitation, reference will be made to a method of assembling the delivery device of FIG. 1 described in detail above.

As embodied herein, the method includes providing a sheath such as sheath 90 depicted herein. However, other types of sheaths may be used. For example, although a bendable sleeve type member has been depicted herein, other forms of sheaths, including sheaths that peel away from a medical device and sheaths that fold over onto themselves when a distal end thereof is pulled proximally may be used.

The method also includes, providing a medical device and disposing the medical device in the sheath. As previously mentioned, different types of medical devices 2 can be provided in accordance with the method of the invention.

When the medical device 400 is provided in the form of a self-expanding stent, the stent is compressed from an expanded state to a compressed state for loading by crimping the stent in a stent-crimping machine. This may be accomplished, for example, by stretching out the distal end 98 of sheath 90 with tweezers, and positioning distal end 98 into the stent crimping machine so that the machine grips the distal end 98 of sheath 90. The stent crimping machine then crimps the stent and advances it proximally into the distal end 98 of sheath 90. After the stent has been loaded, the stretched out portion of the distal end 98 is then trimmed off. The distal end 98 of sheath 90 is provided without a reinforcing layer 114. This is particularly advantageous where the distal end 98 is stretched out to load the stent as described above. Moreover, the medical device disposing step includes placing the medical device 400 into the distal end of the sheath. The medical device disposing step preferably occurs after the bumper positioning step, as described below. It is further contemplated that the medical device 400 may be coated with a lubricious coating such as silicone oil or the like prior to crimping, thereby reducing frictional forces between the medical device and the crimping device as well as frictional forces between the medical device and the sheath. Additionally, the lubricious coating may reduce frictional forces during deployment of the medical device.

The method further includes the steps of providing a nose and placing the sheath through the nose, if desired.

In accordance with this aspect of the invention, sheath 90 is placed through a nose 210 of a handle 120 that is provided, as described above. Preferably, the sheath 90 is placed through the nose 210 prior to positioning the bumper 50 in the sheath 90, as described below. In accordance with another aspect of the invention, the nose providing step additionally includes the steps of providing a stabilizer such as stabilizer 220 and disposing stabilizer 220 on nose 210, if desired.

Even more preferably, if a rotatable actuator is to be provided, shuttle 140 is positioned on the sheath 90 prior to placing the sheath 90 through the nose 210. In this manner, the method further includes the step of positioning the shuttle 140 into a guide member such as shuttle guide 160 as depicted herein.

In further accordance with the invention, the method includes providing a bumper and positioning the bumper into the sheath. For purposes of illustration and not limitation, a bumper such as bumper 50 described herein may be provided. The bumper positioning step further includes the step of positioning bumper 50 into the distal end 98 of the sheath 90. Other variations of bumper 50 described herein are also appropriate for the bumper positioning step.

Additionally, the bumper providing step includes the steps of providing a sleeve member 51 having a cylindrical wall 56, providing a proximal radiopaque portion 76, and placing the proximal radiopaque portion 76 on the sleeve member 51. Proximal radiopaque portion 76 can take various forms, as described in detail above. The bumper providing step also includes the steps of providing a covering member 80 as described in detail above, and disposing covering member 80 on sleeve member 51 and proximal radiopaque portion 76 of bumper 50, if desired.

In still further accordance with the invention the method further includes providing an inner member and placing the inner member through the medical device and the bumper.

For purposes of illustration and not limitation, the inner member placing step generally provides for placing inner member 10 through medical device 400 and bumper 50. Preferably, the inner member placing step occurs after disposing bumper 50 in sheath 90. Even more preferably, the proximal end of the inner member 10 is inserted in the distal end of the sheath.

The inner member placing step also includes positioning the proximal end 12 of the inner member 10 through the medical device 400 and the bumper 50. This is particularly appropriate in the situation where the method also includes the steps of providing a tip 30 and positioning the tip 30 on the distal end 14 of the inner member 10. In this situation, the proximal end 12 of inner member 10 is the only end of inner member 10 that is placed through medical device 400 and bumper 50 since tip 30 has already been attached. The tip providing step can further include the steps of providing a distal radiopaque portion 40 and placing the radiopaque portion on the tip 30. The method can also include the step of annealing the inner member, as described in detail above.

In further accordance with the invention, the method further includes the step of positioning a handle over the inner member.

For purposes of illustration and not limitation, a handle 120 as described in detail above may be provided. In accordance with this aspect of the invention, the handle positioning step includes the steps of providing a thumb screw assembly. The thumb screw assembly 188 of this embodiment includes, for example, a knob 180 and a thumb screw 170. The thumb screw assembly 188 is further positioned on nose 210. The handle positioning step also includes disposing a lock 200 on the thumb screw assembly 188 as described in detail above. The lock 200 preferably snaps into place.

In accordance with another aspect of the invention, the method also includes the step of positioning a hypotube over the proximal end of the inner member.

For purposes of illustration and not limitation, as embodied herein, hypotube 250 is positioned over the proximal end 12 of inner member 10. In accordance with this aspect of the invention, a connector 260 as described above is also provided, disposed coaxially over hypotube 250. The method further includes the step of attaching connector 260 to hypotube 250 by way of an adhesive or other connection.

In accordance with another aspect of the invention, the method further includes the step of applying a lubricious material to the distal end 98 of sheath 90. In accordance with this aspect of the invention, the lubricious material application step preferably occurs when inserting the inner member placing step. For example, when inserting proximal end 12 of inner member 10 through medical device 400 and bumper 50 (where medical device 400 and bumper 50 already having been disposed in sheath 90), a small gap (such as two inches in length) is maintained between proximal end 32 of tip 30 and distal end 98 of sheath. A small amount of lubricant (e.g., two drops of liquid silicone oil) is then applied to distal end 98 of sheath 90. Other suitable liquid lubricants can also be used. A pressurized fluid is then applied to the distal end of the sheath to cause the lubricious material to coat the medical device 400. This step is achieved, for example, by installing a force air fixture over distal end 98 of sheath 90. The force air is activated, and the silicone oil or other lubricant can be seen to migrate along medical device 400, provided that distal end 98 of sheath 90 is made from a transparent material.

In a preferred embodiment, the method further includes the steps of providing an adjustment member 270 configured to move the inner member 10 with respect to the sheath 90 and disposing the adjustment member 270 on the inner member 10. The adjustment member disposing step preferably includes positioning the adjustment member 270 on the proximal end 12 of the inner member 10.

In further accordance with the invention, the method includes the step of applying tension to the inner member.

For purposes of illustration and not limitation, as embodied herein, tension is applied to the proximal end 12 of the inner member 10 to cause the distal end 98 of the sheath 90 to come into physical contact with proximal end of tip 30. The tension applying step is performed after disposing adjustment member 270 over inner member 10, but before attachment of adjustment member 270 to inner member 10. Before attachment of adjustment member 270 to inner member 10, it should be verified that proximal end 32 tip 30 is properly aligned with distal end 98 of sheath 90 and that distal radiopaque portion 4b is flush and aligned with medical device 400. Preferably, thumb screw assembly 188 is positioned over inner member prior to attaching adjusting member to inner core 10, although handle 120 is assembled and attached to delivery system 300 at a later stage if properly configured. Tension may be applied again by the physician upon receipt of the delivery system if inner member 10 lengthens during sterilization or shipping by unlocking adjustment lock 280, and moving adjustment hypotube 272 proximally to bring proximal end 32 of tip 30 into contact with distal end 98 of sheath 90. The method steps need not be practiced in any particular order. The method of the invention can be modified as needed to suit a particular purpose, depending at least in part on the final configuration of the delivery system. For example, handle 120 could be configured so that it is installed last, or thumb screw assembly 188 could be configured such that it is installed after connector 260 is installed.

It will be apparent to those skilled in the art that various modifications and variations can be made in the device, method and system of the present invention without departing from the spirit or scope of the invention. Thus, it is intended that the present invention include modifications and variations that are within the scope of the appended claims and their equivalents.

What is claimed is:

1. A delivery system for delivery of a medical device, the delivery system comprising:
    an inner member having a proximal end and a distal end, the inner member defining a longitudinal axis therebetween;
    a tip disposed at the distal end of the inner member;
    a bumper disposed on the inner member, the bumper having a proximal end and a distal end, a seat being defined between the tip and the distal end of the bumper,
    a sheath disposed about the inner member, the sheath having a proximal end and a distal end, the sheath being movable from a first sheath position substantially covering the seat, and a second sheath position axially offset to expose the seat;
    a handle in contact with the proximal end of the inner member; and
    an actuator on the handle, the actuator including a slider coupled to a rack-and-pinion assembly to move the sheath with respect to the inner member along the longitudinal axis from the first sheath position to the second sheath position, the rack-and-pinion assembly including a rotatable pinion gear operatively coupled with the slider to move the pinion gear in a linear direction.

2. The delivery system of claim 1, wherein the ratio of movement of the sheath to movement of the actuator is greater than 1:1 during at least a portion of movement of the actuator.

3. The delivery system of claim 2, wherein the ratio of movement of the sheath to movement of the actuator varies.

4. The delivery system of claim 2, wherein the ratio of movement of the sheath to movement of the actuator is constant.

5. The delivery system of claim 1 wherein the rack-and-pinion assembly includes a first gear rack, and a second gear rack, wherein the first rack is disposed at an angle relative to the second rack, the first gear rack moveable relative the second gear rack and the pinion gear operatively coupled to the first and second gear racks, respectively.

6. The delivery system of claim 5, wherein the first gear rack is coupled with the sheath.

7. The delivery system of claim 5, wherein the slider is operatively coupled with the pinion gear to engage the pinion gear along the second gear rack to rotate the pinion gear, which in turn engages the first gear rack for linear movement thereof.

8. The delivery system of claim 5, wherein the first rack includes a plurality of gear teeth along a length and the second rack includes a plurality of gear teeth along a length, the first rack having a different number of teeth than the second rack.

9. The system of claim 5 wherein the first rack further comprises pins configured to be received within a track provided on the handle.

10. The delivery system of claim 5, wherein the first gear rack is disposed at an angle less-than ninety degrees relative to the second gear rack.

11. The delivery system of claim 1 wherein the slider has first and second extenders extending therefrom, each extender including a slot defined therein; and further wherein the pinion gear has a first end, second end and a plurality of gear teeth formed therebetween, wherein the first and second ends of the pinion gear slidingly engage a respective one of the slots defined in the first and second extenders;
    the rack-and-pinion assembly further comprising a first rack having a first end and a second end and a plurality of gear teeth formed therebetweeen, the first rack operatively coupled to the pinion gear, and a second rack including a plurality of gear teeth disposed thereon, the plurality of gear teeth of the second rack operatively engaged with the pinion gear, wherein the engagement of the pinion gear along the second rack due to movement of the slider results in movement of the first rack in the linear direction at a rate greater than movement of the slider.

12. The delivery system of claim 11 wherein the plurality of gear teeth disposed on the first rack have a pitch different than the plurality of gear teeth on the second rack.

13. The delivery system of claim 11 wherein the second rack includes a pair of elongate members, each elongate member having a plurality of teeth in engagement with the pinion gear.

14. The delivery system of claim 11 wherein the second rack is arc-shaped.

15. The delivery system of claim 11 wherein the deployment rate of the sheath is at least twice the rate of movement of the actuator.

16. A delivery system for delivery of a medical device, the delivery system comprising:

an inner member having a proximal end and a distal end, the inner member defining a longitudinal axis therebetween;
a tip disposed at the distal end of the inner member;
a bumper disposed on the inner member, the bumper having a proximal end and a distal end, a seat being defined between the tip and the distal end of the bumper;
a sheath disposed about the inner member, the sheath having a proximal end and a distal end, the sheath being movable from a first sheath position substantially covering the seat, and a second sheath position axially offset to expose the seat;
a handle in contact with the proximal end of the inner member; and
an actuator on the handle and coupled to a rack-and-pinion assembly to move the sheath with respect to the inner member along the longitudinal axis from the first sheath position to the second sheath position, the rack-and-pinion assembly including:
a first gear rack,
a second gear rack, and
a slidable pinion gear rotatably coupled between the first gear rack and the second gear rack, the pinion gear being slidable along the second gear rack, which in turn moves the first gear rack in a linear direction.

17. The delivery system of claim 16, wherein the ratio of movement of the sheath to movement of the actuator is greater than 1:1 during at least a portion of movement of the actuator.

18. The delivery system of claim 17, wherein the ratio of movement of the sheath to movement of the actuator varies.

19. The system of claim 16 wherein the first rack further comprises pins configured to be received within a track provided on the handle.

20. The delivery system of claim 16 wherein the second rack is arc-shaped.

* * * * *

UNITED STATES PATENT AND TRADEMARK OFFICE
CERTIFICATE OF CORRECTION

PATENT NO. : 7,780,716 B2
APPLICATION NO. : 11/479607
DATED : August 24, 2010
INVENTOR(S) : Jeffrey Madsen et al.

It is certified that error appears in the above-identified patent and that said Letters Patent is hereby corrected as shown below:

ON THE TITLE PAGE:

--Item (75) Inventors:   Jeffrey Madsen Pappas, Santa Clara, CA (US); Daniel H. Shumer, San Jose, CA (US); Amelia Lasser, Menlo Park, CA (US); Jimmy Jen, Foster City, CA (US); Claus Volkl, Grosselfingen (DE); Juergen Anton Haun, Albstadt (DE)

should read

--Item (75) Inventors:   Jeffrey Madsen Pappas, Santa Clara, CA (US); Daniel H. Shumer, San Jose, CA (US); Amelia Lasser, Menlo Park, CA (US); Jimmy Jen, Foster City, CA (US); Claus Volkl, Grosselfingen (DE); Juergen Anton Hahn, Albstadt (DE)

Signed and Sealed this

Ninth Day of November, 2010

David J. Kappos
*Director of the United States Patent and Trademark Office*